US011293066B2

(12) United States Patent
Chouaib et al.

(10) Patent No.: US 11,293,066 B2
(45) Date of Patent: Apr. 5, 2022

(54) METHOD FOR ASSESSING THE RESPONSE TO PD-1/PDL-1 TARGETING DRUGS

(71) Applicant: INSTITUT GUSTAVE ROUSSY, Villejuif (FR)

(72) Inventors: Salem Chouaib, Bourg la Reine (FR); Stéphanie Buart, Villejuif (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 16/631,848

(22) PCT Filed: Jul. 17, 2018

(86) PCT No.: PCT/EP2018/069332
§ 371 (c)(1),
(2) Date: Jan. 17, 2020

(87) PCT Pub. No.: WO2019/016174
PCT Pub. Date: Jan. 24, 2019

(65) Prior Publication Data
US 2020/0157639 A1 May 21, 2020

(30) Foreign Application Priority Data
Jul. 18, 2017 (EP) .................................... 17305952

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS 11,098,121 B2 * 8/2021 McGranahan ......... G16B 30/00
2016/0312297 A1 10/2016 Ayers et al.

OTHER PUBLICATIONS

Semenza. HIF-1 mediates metabolic responses to intratumoral hypoxia and oncogenic mutations. J Clin Invest. 2013; 123(9):3664-3671. (Year: 2013).*
Lee and Paik. Regulation of BNIP3 in normal and cancer cells. Mol. Cells; 2006; vol. 21, No. 1, pp. 1-6. (Year: 2006).*
Ward et al. Glycogen branching enzyme (GBE1) mutation causing equine glycogen storage disease IV. Mammalian Genome; 2004; 15: 570-577. (Year: 2004).*
Guo et al. Hypoxia induces the expression of the pro-apoptotic gene BNIP3. Cell Death and Differentiation; 2001; 8: 367-376. (Year: 2001).*
Mellor and Harris. The role of the hypoxia-inducible BH3-only proteins BNIP3 and BNIP3L in cancer. Cancer Metastasis Rev; 2007; 26:553-566 (Year: 2007).*
Cody et al. Characterization of the 3p12.3-pcen Region Associated With Tumor Suppression in a Novel Ovarian Cancer Cell Line Model Genetically Modified by Chromosome 3 Fragment Transfer. Molecular Carcinogenesis; 2009; 48:1077-1092. (Year: 2009).*
Bustin and Mueller. Real-time reverse transcription PCR (qRT-PCR) and its potential use in clinical diagnosis. Clinical Science; 2005;109:365-379. (Year: 2005).*
Radke et al. Reference gene stability in peripheral blood mononuclear cells determined by qPCR and NanoString. Microchim Acta; 2014;181:1733-1742. (Year: 2014).*
Malewski et al. RT-PCR technique and its applications. State-of-the-art. Journal of Animal and Feed Sciences; 2003;12:403-416. (Year: 2003).*
Cristescu et al. Pan-tumor genomic biomarkers for PD-1 checkpoint blockade-based immunotherapy. Science; 2018; 362; 197: p. 1-10. (Year: 2018).*
Carbognin et al. Differential Activity of Nivolumab, Pembrolizumab and MPDL3280A according to the Tumor Expression of Programmed Death-Ligand-1 (PD-L1): Sensitivity Analysis. Plos One; 2015; p. 1-16. (Year: 2015).*
Noman et al. Improving Cancer Immunotherapy by Targeting the Hypoxic Tumor microenvironment: New Opportunities and Challenges. Cells; 2019, 8, 1083: p. 1-13. (Year: 2019).*
Chamoto et al. Current issues and perspectives in PD-1 blockade cancer immunotherapy. International Journal of Clinical Oncology; 2020; 25:790-800. (Year: 2020).*
Cristescu et al. Science; 2018; 362; 197; p. 01-12. (Year: 2018).*
Norman et al. Cells 2019, 8, 1083: p. 1-13. (Year: 2019).*
Bryan and Gordon. Blocking tumor escape in hematologic malignancies: The anti-PD-1 strategy. Blood Reviews; 2015; 29; 25-32. (Year: 2015).*
Deeks. Nivolumab: A Review of Its Use in Patients with Malignant Melanoma. Drugs; 2014; 74:1233-1239. (Year: 2014).*
Anonymous, "Human Hypoxia Signaling Pathway PCR Array" Dec. 1, 2012, XP055435880, p. 1, retrieved from the Internet on Dec. 18, 2017: URL:http://www.sabiosciences.com/rt_per_product/HTML/PAHS=032Z.html, Abstract only.
Buart, S. et al. "Transcriptional response to hypoxic stress in melanoma and prognostic potential of GBE1 and BNIP3" *Oncotarget*, Oct. 30, 2017, pp. 108786-108801, vol. 8, No. 65.
Maes, H. et al. "BNIP3 supports melanoma cell migration and vasculogenic mimicry by orchestrating the actin cytoskeleton" *Cell Death and Disease*, Mar. 13, 2014, pp. 1-12, vol. 5, No. 3, e1127.
Noman, M. Z. et al. "Targeting hypoxia at the forefront of anticancer immune responses" *Oncolmmunology*, Dec. 2, 2014, pp. e954463-1-e954463-3, vol. 3, Issue 12.

(Continued)

*Primary Examiner* — Juliet C Switzer
*Assistant Examiner* — Wahwah T Johnson
(74) *Attorney, Agent, or Firm* — Saliwanchik, Lloyd & Eisenschenk

(57) ABSTRACT

The present invention relates to a method for assessing the response to PD-1/PDL-1 targeting drugs based on the differential expression levels of BINP3 and GBE1.

8 Claims, 13 Drawing Sheets

(56) References Cited

OTHER PUBLICATIONS

Semenza, G. L. "HIF-1 mediates metabolic responses to intratumoral hypoxia and oncogenic mutations" *The Journal of Clinical Investigation*, Sep. 3, 2013, pp. 3664-3671, vol. 123, No. 9.
Written Opinion in International Application No. PCT/EP2018/069332, dated Sep. 17, 2018, pp. 1-8.

* cited by examiner

Patient 1

Patient 2

Patient 3

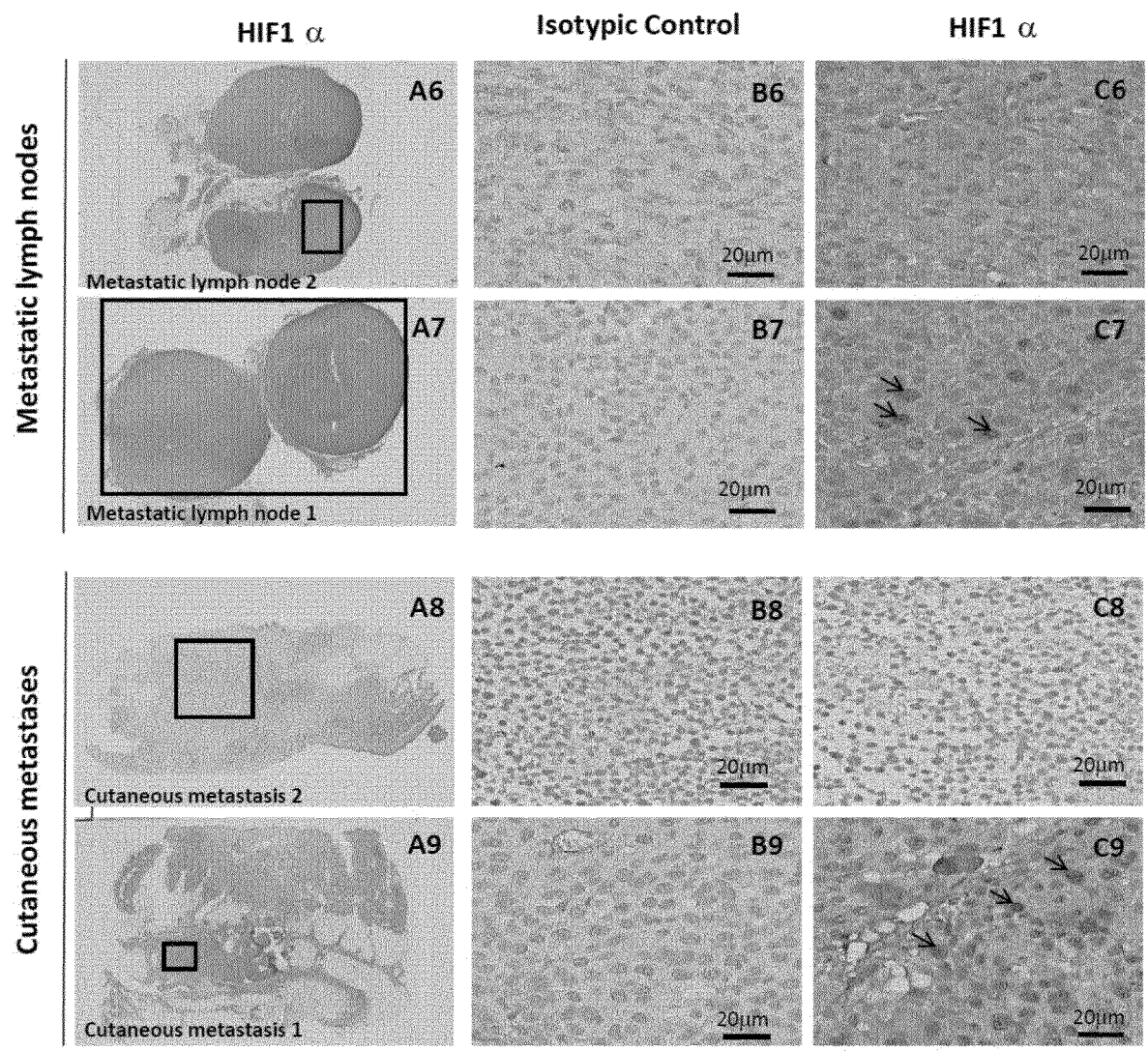
FIGURES 3B & C

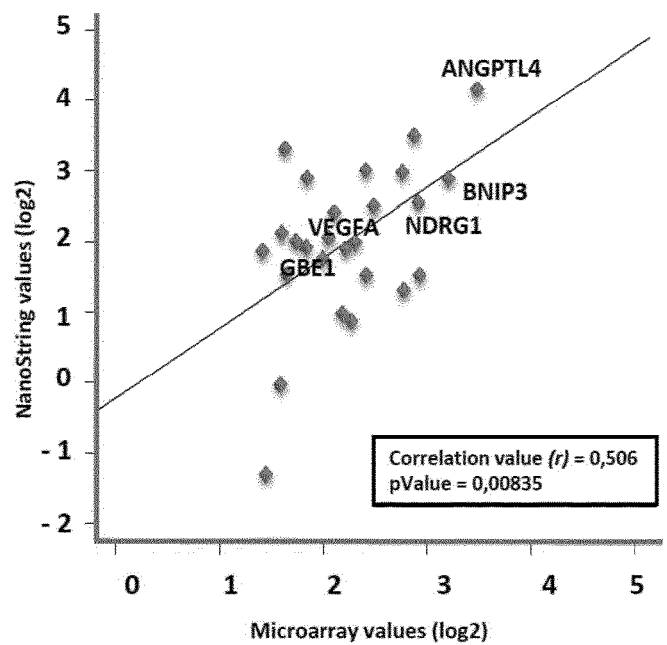
FIGURE 4A
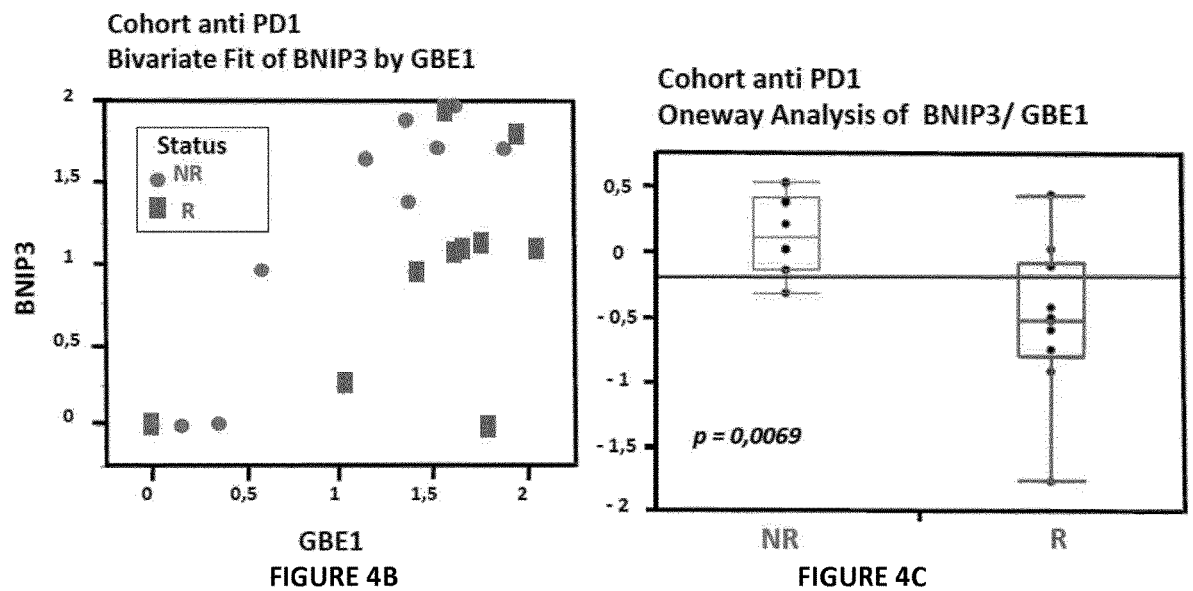
FIGURE 4B
FIGURE 4C

US 11,293,066 B2

METHOD FOR ASSESSING THE RESPONSE TO PD-1/PDL-1 TARGETING DRUGS

CROSS-REFERENCE TO RELATED APPLICATION

This application is the U.S. national stage application of International Patent Application No. PCT/EP2018/069332, filed Jul. 17, 2018.

FIELD OF THE INVENTION

The present invention relates to the fields of genetics, immunology and medicine. The present invention more specifically relates to an in vitro or ex vivo method of assessing the sensitivity of a subject having a cancer to treatment by a PD-1/PD-L1 targeting agent.

BACKGROUND OF THE INVENTION

Tumor cells act on host immunity in several ways to evade immune defenses in the tumor microenvironment. This phenomenon is generally called "cancer immune escape." One of the most important components in this system is an immunosuppressive co-signal (immune checkpoint) mediated by the PD-1 receptor and its ligand, PD-L1. PD-1 is mainly expressed on activated T cells, whereas PD-L1 is expressed on several types of tumor cells. Preclinical studies have shown that inhibition of the interaction between PD-1 and PD-L1 enhances the T-cell response and mediates antitumor activity. Several clinical trials of PD-1/PD-L1 signal-blockade agents have exhibited dramatic antitumor efficacy in patients with certain types of solid or hematological malignancies.

However, the accumulated data from clinical trials for solid tumors revealed that the antitumor response rate of PD-1 inhibitors seems not so high. In addition, PD-1 inhibitors are very expensive and not devoid of adverse reactions. Therefore, it is necessary to identify predictive biomarkers that allow selection of appropriate patients for improving therapeutic efficacy.

SUMMARY OF THE INVENTION

Here, the inventors identified the prognostic and predictive potential of BNIP3 and GBE1 genes in the clinical outcome of subjects treated with anti-PD1 drugs.

The present invention relates to the use of relative expression ratio of BNIP3 to GBE1 as a marker of the sensitivity of a subject having a cancer to a treatment with a PD-1/PD-L1 targeting agent.

Accordingly, the present invention relates to an in vitro method for predicting, assessing or monitoring the sensitivity of a subject having a cancer to a treatment with a PD-1/PD-L1 targeting agent, wherein the method comprises:
  a) determining the expression level of BNIP3 and GBE1 in a cancer sample of the subject; and
  b) determining a relative expression ratio of BNIP3 to GBE1, the relative expression ratio of BNIP3 to GBE1 being indicative of a good responder or a poor responder to a treatment with a PD-1/PD-L1 targeting agent.

Optionally, the method further comprises a step of providing a sample from said subject.

Preferably, the expression level of BNIP3 and GBE1 is determined by measuring the quantity of the mRNA transcripts, for instance by quantitative RT-PCR, real time quantitative RT-PCR, Nanostring technology PCR or by high-throughput sequencing technology such as RNA-Seq or sequencing technologies using microfluidic systems.

In one embodiment, the relative expression ratio of BNIP3 to GBE1 is compared to a relative expression ratio of BNIP3 to GBE1 of reference. Then, a relative expression ratio of BNIP3 to GBE1 higher than the relative expression ratio of BNIP3 to GBE1 of reference is indicative of a poor responder to a treatment with a PD-1/PD-L1 targeting agent and/or a relative expression ratio of BNIP3 to GBE1 lower than the relative expression ratio of BNIP3 to GBE1 of reference is indicative of a good responder to a treatment with a PD-1/PD-L1 targeting agent.

The present invention further relates to an in vitro method for selecting a subject affected with a cancer for a treatment with a PD-1/PD-L1 targeting agent or for determining whether a subject affected with a cancer is susceptible to benefit from a treatment with a PD-1/PD-L1 targeting agent, comprising predicting or assessing the sensitivity of the subject to a treatment with a PD-1/PD-L1 targeting agent by the method according to the present disclosure and selecting a subject as suitable for a treatment with a PD-1/PD-L1 targeting agent if the relative expression ratio of BNIP3 to GBE1 is indicative of a good responder.

In addition, the present invention relates to a PD-1/PD-L1 targeting agent for use in the treatment of a cancer in a subject wherein the subject has a relative expression ratio of BNIP3 to GBE1 indicative of a good responder to a treatment with a PD-1/PD-L1 targeting agent. It relates to the use of a PD-1/PD-L1 targeting agent for the manufacture of a medicine for the treatment of a cancer in a subject who has a relative expression ratio of BNIP3 to GBE1 indicative of a good responder to a treatment with a PD-1/PD-L1 targeting agent. The present invention also relates to a method for treating a subject having a cancer, comprising administering a therapeutic effective amount of a PD-1/PD-L1 targeting agent to the subject if the subject has a relative expression ratio of BNIP3 to GBE1 indicative of a good responder to a treatment with a PD-1/PD-L1 targeting agent.

For instance, the PD-1/PD-L1 targeting agent can be selected from the group consisting of Nivolumab, Pembrolizumab, Pidilizumab, AMP-224, AMP-514, BMS 936559, MPDL3280A, Durvalumab, Avelumab and a combination thereof.

The cancer can be selected in the group consisting of melanoma, lung cancer, ovarian cancer, head and neck cancer, bladder cancer, gastric cancer, renal cancer, colon cancer; esophageal cancer, hepatocellular cancer, breast cancer, hematopoietic cancer such as lymphoma or leukemia, preferably renal cancer, lung cancer, especially non-small-cell lung cancer, melanoma, lymphoma, mesothelioma, colon cancer, pancreatic cancer, breast cancer, melanoma, and glioblastoma, more preferably a melanoma.

Finally, the present invention relates to the use of a kit comprising means for measuring the expression level of BNIP3 and GBE1 such as primers and/or probe specific to BNIP3 and GBE1, for (i) for predicting, assessing or monitoring the sensitivity of a subject having a cancer to a treatment with a PD-1/PD-L1 targeting agent; (ii) for selecting a subject affected with a cancer for a treatment with a PD-1/PD-L1 targeting agent; or (iii) for determining whether a subject affected with a cancer is susceptible to benefit from a treatment with a PD-1/PD-L1 targeting agent.

DETAILED DESCRIPTION

The inventors demonstrate that expression levels of BNIP3 and GBE1 genes can be used as a dual signature to determine if a patient will be a good responder or a poor responder to a treatment with a PD-1/PD-L1 targeting agent. It can be useful for proposing to the patient the most appropriate treatment and for predicting the clinical outcome of the patient.

Definitions

The term "cancer" or "tumor", as used herein, refers to the presence of cells possessing characteristics typical of cancer-causing cells, such as uncontrolled proliferation, immortality, metastatic potential, rapid growth and proliferation rate, and certain characteristic morphological features. This term includes early stage, localized, cancer; later stage, locally advanced cancer; and metastatic stage cancer.

As used herein, the term "marker" and "biomarker" are interchangeable and refer to biological parameters that aid the selection of patients who will benefit from a specific treatment. This term refers particularly to "tumor biomarkers". It is a measurable indicator for predicting the responsiveness of a patient to a specific treatment, in particular a treatment with a PD-1/PD-L1 targeting agent. A biomarker can be found in the blood, urine, stool, tumor tissue, or other tissues or bodily fluids of some patients with cancer, in particular a tumor tissue.

The term "sample", as used herein, means any sample containing cells derived from a subject, preferably a sample which contains nucleic acids. Examples of such samples include fluids such as blood, plasma, saliva, urine, cerebrospinal fluid and seminal fluid samples as well as biopsies, organs, tissues or cell samples. The sample may be treated prior to its use. It may be fresh, frozen or fixed (e.g. formaldehyde or paraffin fixed) sample.

The term "cancer sample" or "tumor sample" refers to any sample containing tumoral cells derived from a patient. Preferably, the sample contains only tumoral cells. In preferred embodiments, the cancer sample is a biopsy or is derived from a biopsy obtained from the patient during surgery.

As used herein, the term "treatment", "therapy", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

By a "therapeutically efficient amount" is intended an amount of therapeutic agent(s) administered to a patient that is sufficient to constitute a treatment of a cancer.

By "good responder" is intended a patient who shows a good therapeutic benefit of the treatment, that is to say a longer disease-free survival, a longer overall survival, a decreased metastasis occurrence, a decreased tumor growth and/or a tumor regression in comparison to a population of patients suffering from the same cancer and having the same treatment.

Alternatively, by "poor responder" is intended a patient who shows a weak therapeutic benefit of the treatment, that is to say a shorter disease-free survival, a shorter overall survival, an increased metastasis occurrence and/or an increased tumor growth in comparison to a population of patients suffering from the same cancer and having the same treatment.

As used herein, the term "poor prognosis" refers to a decreased patient survival and/or an early disease progression and/or an increased disease recurrence and/or an increased metastasis formation. Conversely, the term "good prognosis" refers to an increased patient survival and/or a delayed disease progression and/or a decreased disease recurrence and/or a decreased metastasis formation.

The term "probe", as used herein, means a strand of DNA or RNA of variable length (about 20-1000 bases long) which can be labelled. The probe is used in DNA or RNA samples to detect the presence of nucleotide sequences (the DNA or RNA target) that are complementary to the sequence in the probe.

The term "primer", as used herein, means a strand of short DNA sequence that serves as a starting point for DNA synthesis. The polymerase starts polymerization at the 3'-end of the primer, creating a complementary sequence to the opposite strand. "PCR primers" are chemically synthesized oligonucleotides, with a length between 10 and 30 bases long, preferably about 20 bases long.

The terms "quantity," "amount," and "level" are used interchangeably herein and may refer to an absolute quantification of a molecule in a sample, or to a relative quantification of a molecule in a sample, i.e., relative to another value such as relative to a reference value as taught herein, or to a range of values for the biomarker. These values or ranges can be obtained from a single patient or from a group of patients.

Expression Level of BNIP3 and GBE1 and Relative Expression Ratio of BNIP3 to GBE1

The method as disclosed herein comprises determining the expression level of BNIP3 and GBE1 in a cancer sample of the subject.

BNIP3 gene (Gene ID: 664; UniGene ID: Hs.144873) is encoding BCL2/adenovirus E1B 19 kDa protein-interacting protein 3. The protein is described in UniProtKB under ID Q12983. The amino acid and nucleic sequences of reference are disclosed in Genbank under ID NP_004043.3 and NM_004052.3, respectively.

GBE1 gene ((Gene ID: 2632; UniGene ID: Hs.436062) is encoding 1,4-alpha-glucan-branching enzyme 1. The protein is described in UniProtKB under ID Q04446. The amino acid and nucleic sequences of reference are disclosed in Genbank under ID NP_000149.3. and NM_000158.3, respectively.

A cancer sample may contain a mix of cancer cells and normal cells. When it is the case, a tumor cell enrichment sorting may be performed. Preferably, the cancer sample is a sample containing only cancer cells or at least 70%, preferably 80%, 90%, 95% of cancer cells.

In a preferred embodiment, the above-mentioned method is performed on cancer cells from a cancer sample from said patient.

The above-mentioned method can also necessitate the use of a normal sample, as a way of comparison to the sample, preferably to the cancer sample. The normal sample can be a sample from the same patient or from another patient. The normal sample can also be from another patient, preferably a normal or healthy patient, i.e. a patient who does not suffer from a cancer.

The above-mentioned method may also comprise a step of obtaining or providing a sample from said patient.

The expression level of BNIP3 and GBE1 may be determined by any method known by the skilled person. In particular, expression level may be determined by measuring the quantity of mRNA.

Methods for determining the quantity of mRNA are well known in the art and include, but are not limited to, quantitative or semi-quantitative RT-PCR, real time quantitative or semi-quantitative RT-PCR, Nanostring technology, sequencing based approaches, for instance by high-throughput sequencing technology such as RNA-Seq or sequencing technologies using microfluidic systems, or transcriptome approaches.

The nucleic acid contained in the sample (e.g., cells or tissue prepared from the patient) may be first extracted according to standard methods, for example using lytic enzymes or chemical solutions or extracted by nucleic-acid-binding resins following the manufacturer's instructions. These nucleic acids may be frozen to be stored before use.

The extracted mRNA may be then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous. Preferably, primer pairs were designed in order to overlap an intron, so as to distinguish cDNA amplification from putative genomic contamination. Such primers may be easily designed by the skilled person. Other methods of Amplification include, but are not limited to, ligase chain reaction (LCR), transcription-mediated amplification (TMA), strand displacement amplification (SDA) and nucleic acid sequence based amplification (NASBA).

Alternatively, the quantity of mRNA may also be measured using the Nanostring's NCOUNTER™ Digital Gene Expression System (Geiss et al. 2008 Nat. Biotechnol. 26:317-325) which captures and counts individual mRNA transcripts by a molecular bar-coding technology and is commercialized by Nanostring Technologies, or the QuantiGene® Plex 2.0 Assay (Affymetrix).

The quantity of mRNA may further be determined using approaches based on high-throughput sequencing technology such as RNA-Seq (Wang et al. Nat Rev Genet. 2009 January; 10(1): 57-63) or sequencing technologies using microfluidic systems.

The expression level of a gene may also be determined by measuring the quantity of mRNA by transcriptome approaches, in particular by using DNA microarrays. To determine the expression level of a gene, the sample, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling.

Many variants of the microarray hybridization technology are available to the man skilled in the art. Examples of DNA biochips suitable to measure the expression level of the genes of interest include, but are not limited to, Human Genome U133 Plus 2.0 array (Affymetrix).

Next Generation Sequencing methods (NGS) may also be used.

In a particular embodiment, the quantity of mRNA is measured by quantitative RT-PCR.

Preferably, expression levels of genes BNIP3 and GBE1 are normalized to a reference expression level, preferably to the expression level of one or more housekeeping (or control or reference) genes.

As used herein, the term "housekeeping gene" refers to a gene involved in basic functions needed for maintenance of the cell. Housekeeping genes are transcribed at a relative constant level and are thus used to normalize expression levels of genes that vary across different samples. Examples of housekeeping genes include, but are not limited to, GAPDH (Gene ID NCBI 2597), ribosomal 18S gene (RNA18S5, Gene ID NCBI: 100008588), beta-glucuronidase, b-actin (ACTB), peptidylprolyl isomerase A (cyclophilin A, PPIA), tubulin, ubiquitin, RPLPO, HPRT1 and B2M genes.

In a particular embodiment, the expression level of each gene is determined by measuring the amount of mRNA by quantitative RT-PCR and is normalized with respect to that of a housekeeping gene, preferably the peptidylprolyl isomerase A (cyclophilin A, PPIA), b-actin (ACTB), and Glyceraldehyde-3-phosphate dehydrogenase (GAPDH) reference genes, by the $2^{-\Delta Ct}$ method.

In one preferred embodiment, expression levels of BNIP3 and GBE1 are determined by quantitative RT-PCR and the relative expression ratio of BNIP3 to GBE1 can be obtained by the method commonly known as the ΔΔCt method:

$$\Delta\Delta Ct(BNIP3/GBE1 \text{ relative expression ratio})=\Delta Ct(BNIP3)-\Delta Ct(GBE1)$$

where
ΔCt (BNIP3)=Ct (BNIP3 gene in the cancer sample from the subject)–Ct (housekeeping gene in the cancer sample from the subject), and
ΔCt (GBE1)=Ct (GBE1 gene in the cancer sample from the subject)–Ct (housekeeping gene in the cancer sample from the subject).

In another preferred embodiment, expression levels of BNIP3 and GBE1 are determined using techniques allowing direct quantification of each RNA molecule in a given sample (e.g. nanostring or microfluidic PCR). More particularly, expression levels of BNIP3 and GBE1 are determined using techniques allowing direct quantification of each RNA molecule in a given sample (e.g. nanostring or microfluidic PCR) and the BNIP3/GBE1 relative expression ratio in the cancer sample from a subject may be obtained using the following calculation:

BNIP3/GBE1 relative expression ratio=|RNA quantity of BNIP3 in the cancer sample from the subject–RNA quantity of GBE1 in the cancer sample from the subject| wherein RNA quantities are preferably normalized with the RNA quantities of one, two or three housekeeping genes.

BNIP3/GBE1 relative expression ratio determined in a subject sample is then compared to a BNIP3/GBE1 relative expression ratio of reference.

The BNIP3/GBE1 relative expression ratio of reference is determined based on a patient cohort comprising good responders and poor responders to a treatment with a PD-1/PD-L1 targeting agent. This BNIP3/GBE1 relative expression ratio of reference corresponds to the threshold between a good responder and a poor responder. The methods for determining the threshold between a good responder and a poor responder is well-known to the person skilled in the art.

The inventors determined that, if the BNIP3/GBE1 relative expression ratio in a subject sample is higher that the BNIP3/GBE1 relative expression ratio of reference (i.e., if BINP3 expression level is higher or GBE1 expression level lower), then it is indicative of a poor responder status to a PD-1/PD-L1 targeting agent. If the BNIP3/GBE1 relative expression ratio in a subject sample is lower that the BNIP3/GBE1 relative expression ratio of reference (i.e., if BINP3 expression level is lower or GBE1 expression level higher), then it is indicative of a good responder status to a PD-1/PD-L1 targeting agent.

For instance, the relative expression ratio of BNIP3 to GBE1 in a population of poor and good responders is studied as follow. The expression data of GBE1 are used as the X-axis and the expression data of BNIP3 as Y-axis. The expression data of BNIP3 and GBE1 of a population comprising good responders and poor responders can be used to calculate the formula of Y and X relationship. The slope can be the relative expression ratio of BNIP3 to GBE1 of reference (see FIG. 4B). Accordingly, a relative expression ratio of BNIP3 to GBE1 higher than the relative expression ratio of BNIP3 to GBE1 of reference is indicative of poor responder status. On the opposite, a relative expression ratio of BNIP3 to GBE1 lower than the relative expression ratio of BNIP3 to GBE1 of reference is indicative of poor responder status.

Alternatively, the BNIP3/GBE1 relative expression ratio of reference can be determined by other statistical methods. For instance, a cluster analysis can be performed.

Therefore, the present invention relates to the use of relative expression ratio of BNIP3 to GBE1 as a marker of the sensitivity of a subject having a cancer to a treatment with a PD-1/PD-L1 targeting agent.

Subject Susceptible to Benefit from a Treatment with a PD-1/PD-L1 Targeting Agent The present invention provides a method for determining if a subject having a cancer is a good responder or a poor responder to a treatment with a PD-1/PD-L1 targeting agent based on the BNIP3/GBE1 relative expression ratio.

Accordingly, the present invention relates to a method for selecting a subject affected with a cancer for a treatment with a PD-1/PD-L1 targeting agent or for determining whether a subject affected with a cancer is susceptible to benefit from a treatment with a PD-1/PD-L1 targeting agent. The method comprises determining the BNIP3/GBE1 relative expression ratio in a cancer sample of the subject as described above and determining if the BNIP3/GBE1 relative expression ratio is indicative of a good responder or a poor responder.

The method may further comprise the step of selecting the subject if the BNIP3/GBE1 relative expression ratio is indicative of a good responder and optionally administering the selected subject a therapeutically effective amount of a PD-1/PD-L1 targeting agent.

It may also further comprise the step of selecting the subject as not suitable to benefit to a treatment with a PD-1/PD-L1 targeting agent if the BNIP3/GBE1 relative expression ratio is indicative of a poor responder. This subject can be selected for an alternative treatment either with a treatment without any PD-1/PD-L1 targeting agent or with a combination treatment comprising a PD-1/PD-L1 targeting agent and another antitumoral drug.

Therefore, the present invention provides a new group of subjects having a cancer for the treatment by a PD-1/PD-L1 targeting agent. Indeed, the new group of subjects is defined by its BNIP3/GBE1 relative expression ratio. The BNIP3/GBE1 relative expression ratio is indicative of a good responder to a treatment by a PD-1/PD-L1 targeting agent. More specifically, the new group of subjects has a BNIP3/GBE1 relative expression ratio lower than the BNIP3/GBE1 relative expression ratio of reference.

Accordingly, the present invention relates to a PD-1/PD-L1 targeting agent for use in the treatment of a cancer in a subject, wherein the subject has a relative expression ratio of BNIP3 to GBE1 indicative of a good responder to a treatment with a PD-1/PD-L1 targeting agent. The present invention also relates to the use of a PD-1/PD-L1 targeting agent for the manufacture of a medicine for the treatment of a cancer in a subject who has a relative expression ratio of BNIP3 to GBE1 indicative of a good responder to a treatment with a PD-1/PD-L1 targeting agent.

More particularly, the BNIP3/GBE1 relative expression ratio lower than the BNIP3/GBE1 relative expression ratio of reference. The status regarding relative expression ratio of BNIP3 to GBE1 can be determined in a sample from the subject by the method as detailed above.

The present invention further relates to a method for treating a subject having a cancer, comprising administering a therapeutic effective amount of a PD-1/PD-L1 targeting agent to the subject if the subject has a relative expression ratio of BNIP3 to GBE1 indicative of a good responder to a treatment with a PD-1/PD-L1 targeting agent. The method may comprise determining the relative expression ratio of BNIP3 to GBE1 of the subject, administering a therapeutic effective amount of a PD-1/PD-L1 targeting agent to the subject if the subject has a relative expression ratio of BNIP3 to GBE1 indicative of a good responder to a treatment with a PD-1/PD-L1 targeting agent.

Cancer

The method above-mentioned and the PD-1/PD-L1 targeting agent for use can be used to guide treatment for any appropriate cancer. In one embodiment, the cancer is a hematopoietic cancer. In another embodiment, the cancer is a solid tumor. In various embodiments, the cancer comprises an acute lymphoblastic leukemia; acute myeloid leukemia; adrenocortical carcinoma; AIDS-related cancer; AIDS-related lymphoma; anal cancer; appendix cancer; astrocytomas; atypical teratoid/rhabdoid tumor; basal cell carcinoma; bladder cancer; brain stem glioma; brain tumor, brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma; breast cancer; bronchial tumors; Burkitt lymphoma; cancer of unknown primary site (CUP); carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor. The cancer can include without limitation an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumor (GIST), glioblastoma, head and neck squamous carcinoma, leukemia, liver hepatocellular carcinoma, low grade glioma, lung bronchioloalveolar carcinoma (BAC), non-small cell lung cancer (NSCLC), lung small cell cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non-epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma.

In some embodiments, the cancer comprises a breast cancer, triple negative breast cancer, metaplastic breast cancer (MpBC), head and neck squamous cell carcinoma (HNSCC), human papilloma virus (HPV)-positive HNSCC, HPV-negative/TP53-mutated HNSCC, metastatic HNSCC, oropharyngeal HNSCC, non-oropharyngeal HNSCC, a carcinoma, a sarcoma, a melanoma, a luminal A breast cancer, a luminal B breast cancer, HER2+ breast cancer, a high microsatellite instability (MSI-H) colorectal cancer, a microsatellite stable colorectal cancer (MSS), non-small cell lung cancer (NSCLC), chordoma, or adrenal cortical carcinoma. The carcinoma can be a carcinoma of the breast, colon, lung, pancreas, prostate, Merkel cell, ovary, liver, endometrial, bladder, kidney or cancer of unknown primary (CUP). The sarcoma can be a liposarcoma, chondrosarcoma, extraskeletal myxoid chondrosarcoma or uterine sarcoma. In some embodiments, the sarcoma comprises an alveolar soft part sarcoma (ASPS), angiosarcoma, breast angiosarcoma, chondrosarcoma, chordoma, clear cell sarcoma, desmoplastic small round cell tumor (DSRCT), epithelioid hemangioendothelioma (EHE), epithelioid sarcoma, endometrial stromal sarcoma (ESS), ewing sarcoma, fibromatosis, fibrosarcoma, giant cell tumour, leiomyosarcoma (LMS), uterine LMS, liposarcoma, malignant fibrous histiocytoma (MFH/UPS), malignant peripheral nerve sheath tumor (MPNST), osteosarcoma, perivascular epithelioid cell tumor (PEComa), rhabdomyosarcoma, solitary fibrous tumor (SFT), synovial sarcoma, fibromyxoid sarcoma, fibrous hamartoma of infancy, hereditary leiomyomatosis, angiomyolipoma, angiomyxoma, atypical spindle cell lesion (with fibrohistiocytic differentiation), chondroblastoma, dendritic cell sarcoma, granular cell tumor, high grade myxoid sarcoma, high-grade myoepithelial carcinoma, hyalinizing fibroblastic sarcoma, inflammatory myofibroblastic sarcoma, interdigitating dendritic cell tumor, intimal sarcoma, leiomyoma, lymphangitic sarcomatosis, malignant glomus tumor, malignant myoepithelioma, melanocytic neoplasm, mesenchymal neoplasm, mesenteric glomangioma, metastatic histocytoid neoplasm, myoepithelioma, myxoid sarcoma, myxoid stromal, neurilemmoma, phyllodes, rhabdoid, round cell, sarcoma not otherwise specified (NOS), sarcomatous mesothelioma, schwannoma, spindle and round cell sarcoma, spindle cell or spinocellular mesenchymal tumor.

In one embodiment, the cancer can be selected in the group consisting of melanoma, lung cancer, ovarian cancer, head and neck cancer, bladder cancer, gastric cancer, renal cancer, colon cancer; esophageal cancer, hepatocellular cancer, breast cancer, hematopoietic cancer such as lymphoma or leukemia.

In a preferred embodiment, the cancer is selected from the group consisting of renal cancer, lung cancer, especially non-small-cell lung cancer, melanoma, lymphoma, mesothelioma, colon cancer, pancreatic cancer, breast cancer, melanoma, and glioblastoma.

Optionally, the cancer may be selected from the group consisting of non-small-cell lung cancer, melanoma, and renal-cell cancer.

In a preferred embodiment, the cancer is a melanoma.

PD-1/PD-L1 Targeting Agents

The present invention relates to cancer treatment with PD-1/PD-L1 targeting agents. The PD-1/PD-L1 targeting agent can be a molecule targeting PD-L1, a molecule targeting PD-1 or a molecule targeting the PD-1/PD-L1 complex. Preferably, the PD-1/PD-L1 targeting agent is a molecule targeting PD-1 or the PD-1/PD-L1 complex. More preferably, the PD-1/PD-L1 targeting agent is a PD-1 antagonist or a PD-1/PD-L1 antagonist.

"PD-1 antagonist" or "PD-1/PDL-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 (Programmed cell death protein 1) and its ligands include: PDCD1, PD1, CD279 and SLEB2 for PD-1; PDCD1L1, PDL1, B7H1, B7-4, CD274 and B7-H for PD-L1 (Programmed death-ligand 1); and PDCD1L2, PDL2, B7-DC, Btdc and CD273 for PD-L2 (Programmed death-ligand 2). In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP 054862 and NP_079515, respectively.

PD-1 antagonists useful in the any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgGI, IgG2, IgG3 and IgG4 constant regions, and in preferred embodiments, the human constant region is an IgGI or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,521,051, 8,008, 449, and 8,354,509. Specific anti-human PD-1 mAbs useful as the PD-1 antagonist in the various aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6, nivolumab (BMS-936558), a human IgG4 mAb with the structure described in WHO Drug Information, Vol. 27, No. 1, pages 68-69 (2013) and which comprises the heavy and light chain amino acid sequences shown in FIG. 7; pidilizumab (CT-011, also known as hBAT or liBAT-1); and the humanized antibodies h409Al I, h409A16 and h409A17, which are described in WO2008/156712.

Examples of mAbs that bind to human PD-L1, and useful in any of the various aspects and 1 embodiments of the present invention, are described in WO2013/019906, WO2010/077634 A1 and U.S. Pat. No. 8,383,796. Specific anti-human PD-L1 mAbs useful as the PD-L1 antagonist in the various aspects and embodiments of the present invention include MPDL3280A, BMS-936559, MED14736, MSB0010718C and an antibody which comprises the heavy chain and light chain variable regions of SEQ ID NO:24 and SEQ ID NO:21, respectively, of WO2013/019906.

Other PD-1 antagonists useful in any of the various aspects and embodiments of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, compositions and uses of the present invention include AMP-224 (also known as B7-DCIg), which is a PD-L2-FC fusion protein and binds to human PD-1.

The PD-1 antagonist can be selected among a PD-1 modulating therapy, PD-1 inhibitor, anti-PD-1 immunotherapy, anti-PD-1 monoclonal antibody, a PD-1 ligand soluble construct, and/or AMP-224 (Amplimmune); performing protein analysis on PD-L1 to determine likely benefit or lack of benefit from a PD-L1 modulating therapy, PD-L1 inhibitor, anti-PD-L1 immunotherapy, anti-PD-L1 monoclonal antibody, BMS-936559, MPDL3280A/ RG7446, and/or MEDI4736 (MedImmune).

In a preferred embodiment, the PD-1 antagonist is selected from the group consisting of Nivolumab (Opdivo, Bristol-Myers Squibb), Pembrolizumab (Keytruda, MK-3475, Merck), Pidilizumab (CT-011, Cure Tech), AMP-224 (Amplimmune/GlaxoSmith Klien), AMP-514 (Amplimmune/GlaxoSmith Klien), BMS 936559 (Bristol Myers Squibb), MPDL3280A (Atezolizumab, Roche), Durvalumab (MPDL14736, MedImmune/AstraZeneca), Avelumab (MSB0010718C, Merck Serono/Pfizer) and a combination thereof, preferably from the group consisting of Nivolumab (Opdivo, Bristol-Myers Squibb), Pembrolizumab (Keytruda, MK-3475, Merck), Pidilizumab (CT-011, Cure Tech), BMS 936559 (Bristol Myers Squibb), MPDL3280A (Roche), RG7446 (Genentech—Hoffmann-La Roche), MED14736 (AstraZeneca) AMP-514 (MedImmune) and AMP-224 (GlaxoSmithKline).

In a most preferred embodiment, the PD-1 antagonist is selected from the group consisting of Nivolumab (Opdivo, Bristol-Myers Squibb), Pembrolizumab (Keytruda, MK-3475, Merck), Pidilizumab (CT-011, Cure Tech), BMS 936559 (Bristol Myers Squibb), and MPDL3280A (Roche).

Kit and Use of a Kit

The present invention relates to a kit comprising means suitable for determining the expression levels of BNIP3 and GBE1 genes and its use for (i) for predicting, assessing or monitoring the sensitivity of a subject having a cancer to a treatment with a PD-1/PD-L1 targeting agent; (ii) for selecting a subject affected with a cancer for a treatment with a PD-1/PD-L1 targeting agent; or (iii) for determining whether a subject affected with a cancer is susceptible to benefit from a treatment with a PD-1/PD-L1 targeting agent.

For instance, the means suitable for determining the expression levels of BNIP3 and GBE1 genes can be primers and/or probe specific to BNIP3 and GBE1 genes.

Figure 1A:
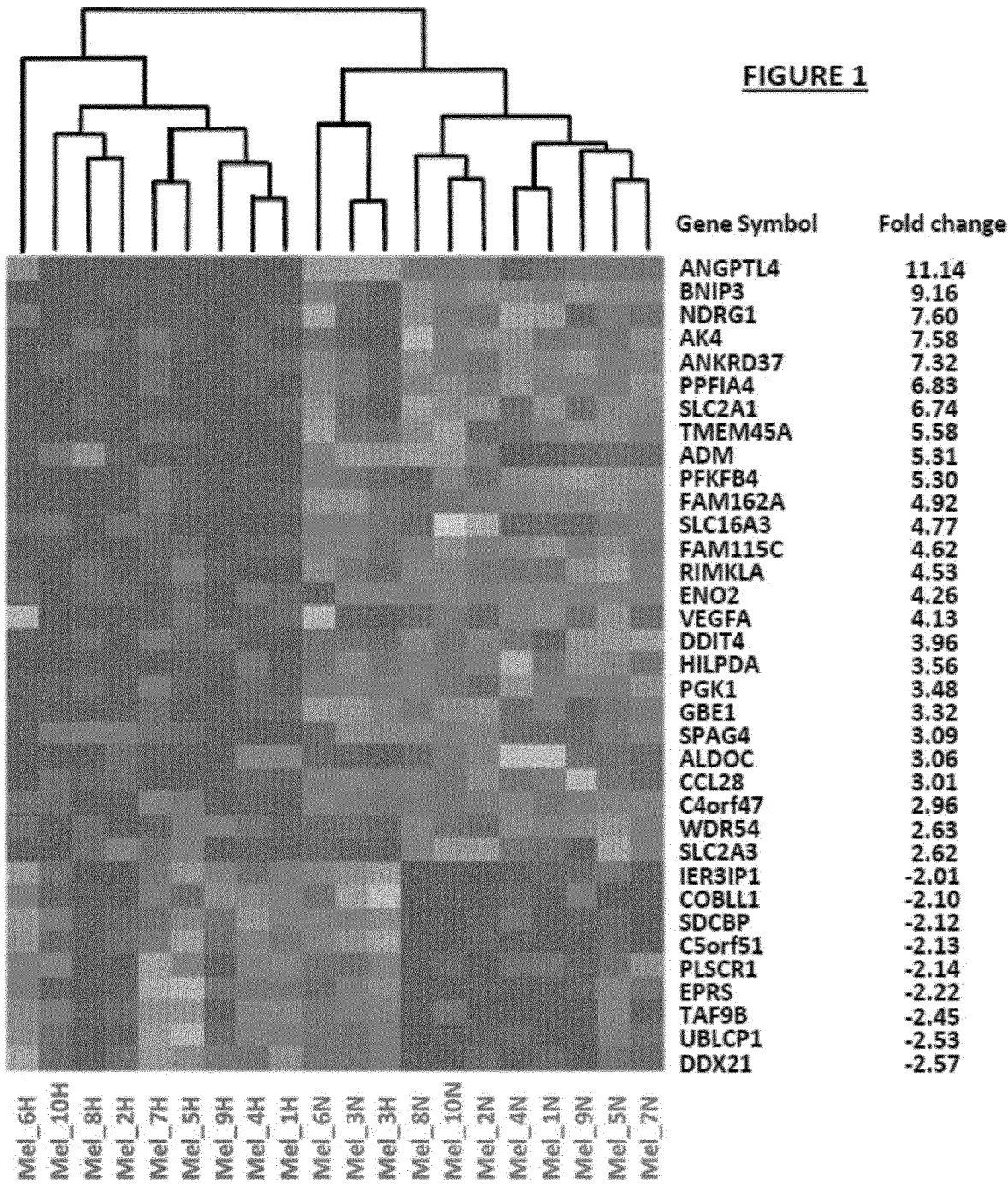
FIG. 1. Hypoxic genes expression profiles in 10 primary human cell lines.

The Hypomel signature was restricted at 26 genes overexpressed with FC≥2.50 and 9 genes underexpressed FC≤−2 with a pValue<0.005. Expression levels for individual genes were scaled by red or green color indicating an elevated or suppressed level of expression, respectively.

(FIG. 1A) Heat map of the 35 hypoxia regulated genes in 10 primary human melanoma cell lines, associated with gene symbol and fold change microarray data after 24 h hypoxia (1% 02).

(FIG. 1B) Representation of correlation hypoxia 24 h versus normoxia fold change for microarray data, PCR1 data and PCR2 data for Hypomel 35 genes.

(FIG. 1C) Correlation fold change between Microarray data (fold change) and PCR data: average of two independent RT-pPCR experiments (PCR1 and PCR2).

(FIG. 1D) Hypomel genes expression in PBMC by RT-qPCR.

Representation of correlation data hypoxia 24 h versus normoxia fold change for two independent PCR1 and PCR2 for hypomel 35 genes in PBMC.

FIG. 2.

Quantification by RT-qPCR of Hypomel 35 genes signature in 3 couples of primary and metastatic cell lines from 3 patients.

(FIG. 2A) Patient 1 from which were derived primary cell line Ray 12 and metastatic cell line M1.

(FIG. 2B) Patient 2 from which were derived primary cell line T1 and metastatic cell line G1.

(FIG. 2C) Patient 3 from which were derived primary cell line M4T and metastatic cell line M4T2.

The 35 genes were quantified in two independent experiments twice after reverse transcription of total extraction mRNA from cells cultivated in normoxia and hypoxia 24 h.

Quantification by western-blot of 3 proteins highly induced in hypoxia 16 h, 24 h and 48 h (HIF1a, ANGPTL4 and BNIP3) versus actin in 3 couples of primary and metastatic cell lines from 3 patients.

(FIG. 2D) Patient 1 from which were derived primary cell line Ray 12 and metastatic cell line M1.

(FIG. 2E) Patient 2 from which were derived primary cell line T1 and metastatic cell line G1.

(FIG. 2F) Patient 3 from which were derived primary cell line M4T and metastatic cell line M4T2.

FIG. 3. Hypoxia associated gene expression in hypoxic zone detected by anti-HIF1a immunohistochemistry (IHC) of melanoma patients.

(FIG. 3A) IHC identification of 4 hypoxic (C2, C3, C4, C5) and 1 non hypoxic zone (C1), delimited in rectangle in A1 to A5, in primary melanoma from 4 patients: detection of HIF1a on serial sections of FFPE tissues. A1 and A2 is the same primary melanoma with one hypoxic zone (A2) and one non hypoxic zone (A1).

Specific staining is observed in C2 (as compared with C1) in tumor nuclei (arrows). C3, C4 and C5 also show nuclear staining (arrows) with a variable cytoplasmic staining considered as non specific.

(FIGS. 3B & C) IHC Identification of hypoxic (C7 and C9) and non hypoxic (C6 and C8) zones, delimited in rectangle in A6 to A9 in 2 metastatic lymph nodes (A6 and A7) and 2 cutaneous metastases (A8 and A9) from 4 patients: detection of HIF1a by IHC on serial sections of FFPE tissues.

Magnification ×20 in A. Magnification ×400 in B and C.
A1 to A9 and C1 to C9: immunostaining with anti-HIF1a, B1 to B9: immunostaining with isotypic control.

Hypomel Genes Expression in FFPE Hypoxia Zone Positive Macro or Micro Dissected from 8 Patients by RT-qPCR.

(FIG. 3D) 4 patients with primary melanomas.
(FIG. 3E) 2 patients with metastatic lymph nodes.
(FIG. 3F) 2 patients with cutaneous metastases.

Representation of correlation data HIF positive zone versus HIF negative zone fold change.

The average of transcripts levels of PPIA, GAPDH and ACTB were used as endogenous controls genes.

FIG. 4. Hypoxia associated gene expression in a cohort of 20 FFPE tumors from melanoma patients treated with anti PD1:

(FIG. 4A) Comparison of gene expression values generated by microarray and NanoString® for a total of 8 RNA samples:

6 RNA samples extracted from 3 cell lines cultivated in normoxia and hypoxia Mel_1, Mel_6 and Mel_10.

1 RNA sample extracted from hypoxia FFPE zone positive of a primary melanoma (zone A4, FIG. 3).

1 RNA sample extracted from hypoxia FFPE zone negative of a primary melanoma (zone A1, FIG. 3).

Correlation of gene expression values for the 8 samples, (correlation value (r)=0.506, p value=0.00835).

(FIG. 4B) and (FIG. 4C) Transcriptional analysis by technology NanoString® and data analysed by statistic method based on differential pair analysis: correlation between expression of hypoxia genes GBE1/BNIP3 in tumors and response to treatment anti PD1.

The cohort anti PD1 regroups a total of 20 patients: 10 patients responders (R) and 10 patients no responders (NR) to treatment anti PD1, significant difference between NR and R for expression GBE1/BNIP3, (P=0.0069).

EXAMPLES

Results

Transcriptional Changes Associated with Hypoxia on Primary Melanoma

Figure 1B:
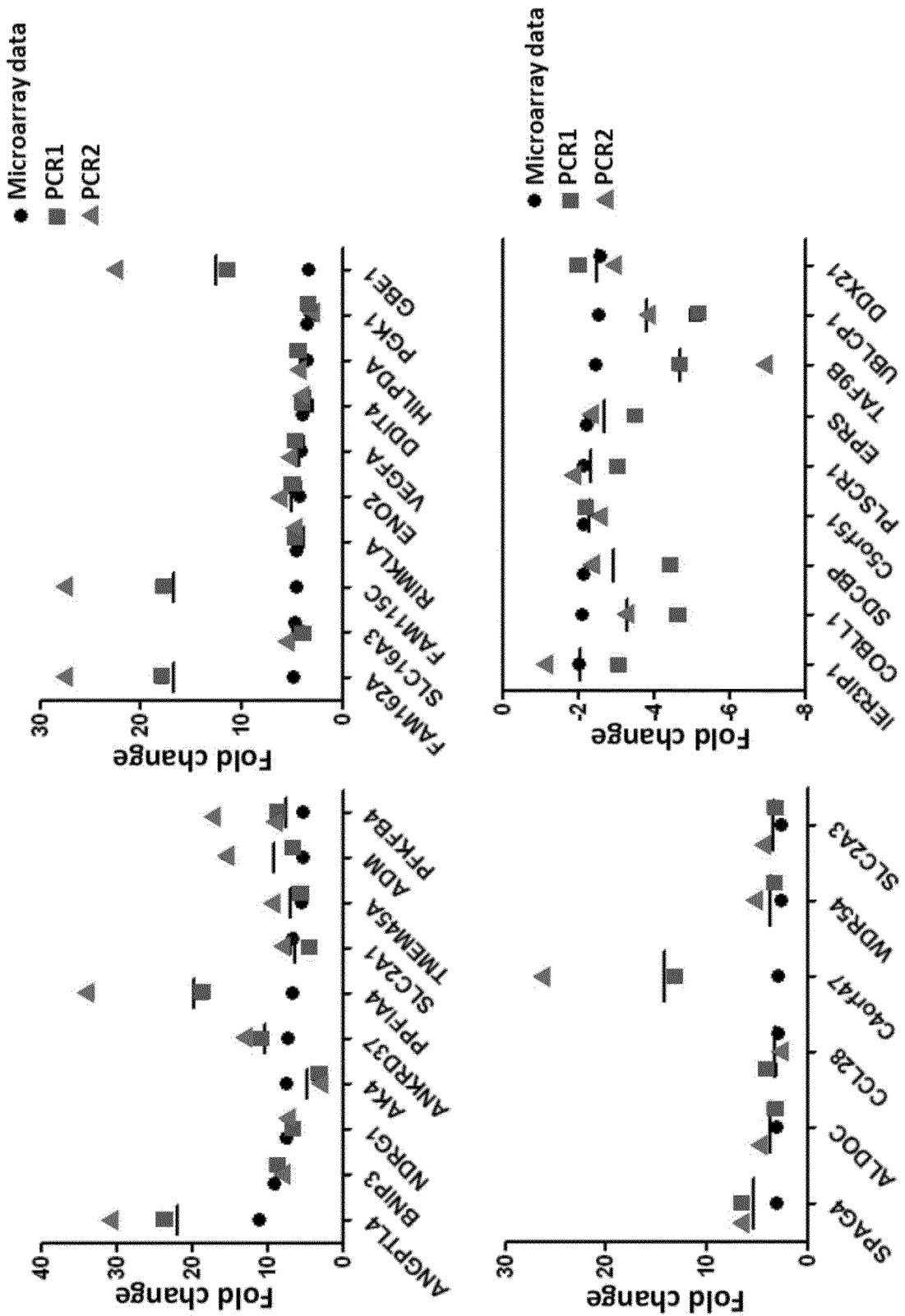
Figure 1C:
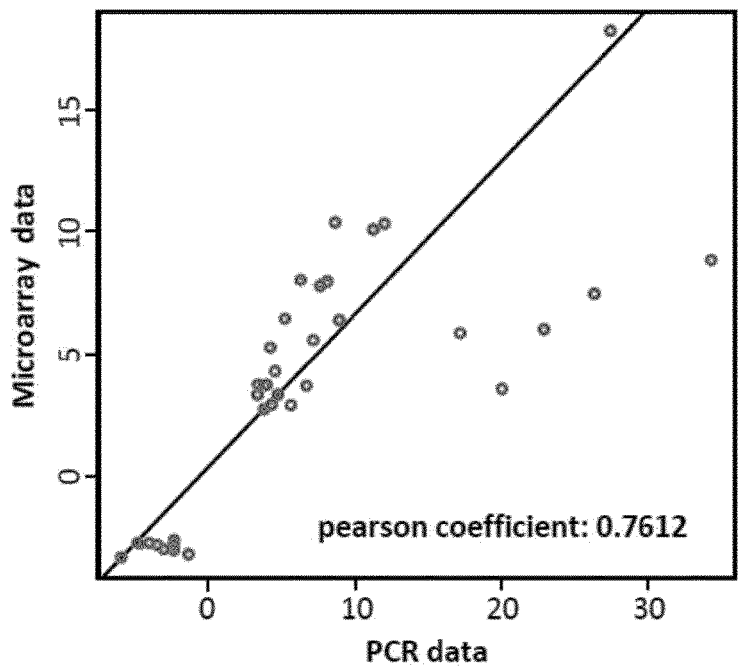
Figure 1D:
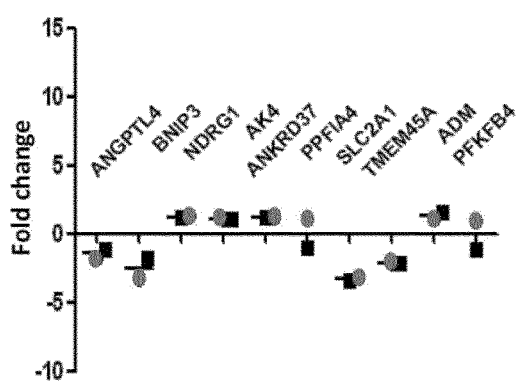
Figure 1D:
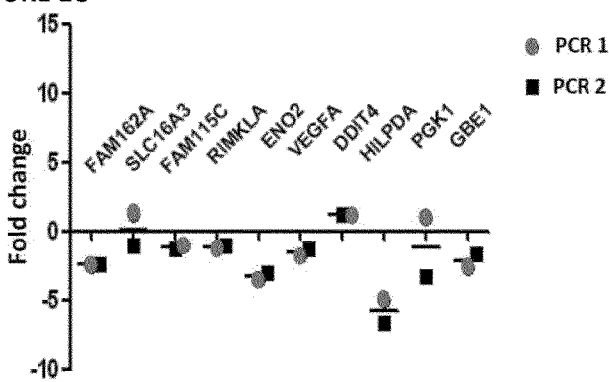
Figure 1D:
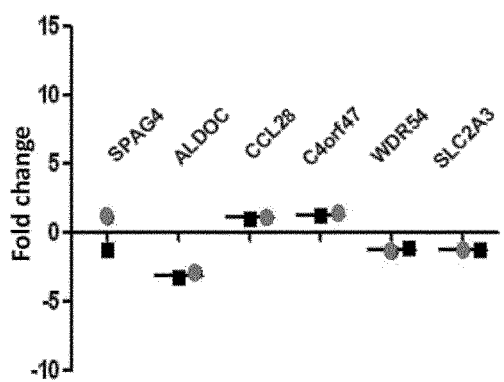
Figure 1D:
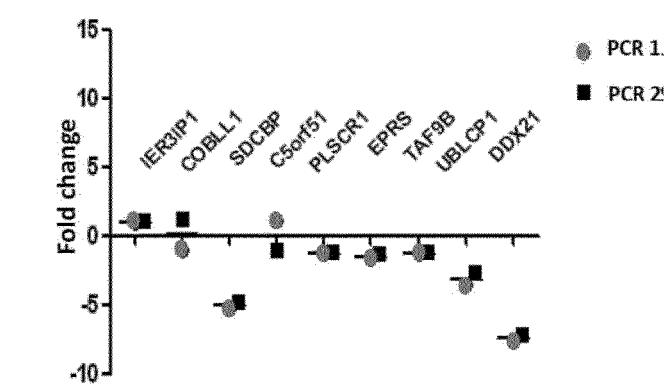

The inventors analyzed the changes in global transcript level in response to hypoxia stress. For this purpose, they used DNA microarrays to examine the gene expression program in response to hypoxia (1% $O_2$) in different melanoma cell lines established from melanoma patients. They profiled global mRNA levels at a time point (24 h). The different mRNA samples were analyzed by hybridization to DNA microarrays. Analysis with microarray assay (AGILENT SurePrint G3 Human GE 8×60K Microarray, Agilent Technologies, AMADID 28004) of gene expression profile of human primary cell lines of melanoma cultured at 1% oxygen versus 21% oxygen, permitted to establish a signature of 35 genes (FIG. 1A). 26 genes up regulated (fold-change≥2.5) and 9 genes down regulated under hypoxic conditions (fold change≤−2) and an adjusted p-value (FDR) <0.05. Cluster data analysis indicates that these genes belong to different pathways (FIG. 1A and table 1). The inventors next performed PCR analysis (PCR1 and PCR2) and confirmed the expression of hypoxia associated genes identified (FIG. 1B). The data of the microarray correlated with data obtained by RT-qPCR from two independent experiment analyses of the 35 gene expression in each of the tested 10 human cell lines. A correlation fold change for microarray data and RT-qPCR is depicted in FIG. 1C. Data depicted in FIG. 1D indicate that the genes associated with hypoxic stress are specifically induced in melanoma and not in peripheral blood lymphocytes cultured under hypoxic conditions.

Figure 2A:
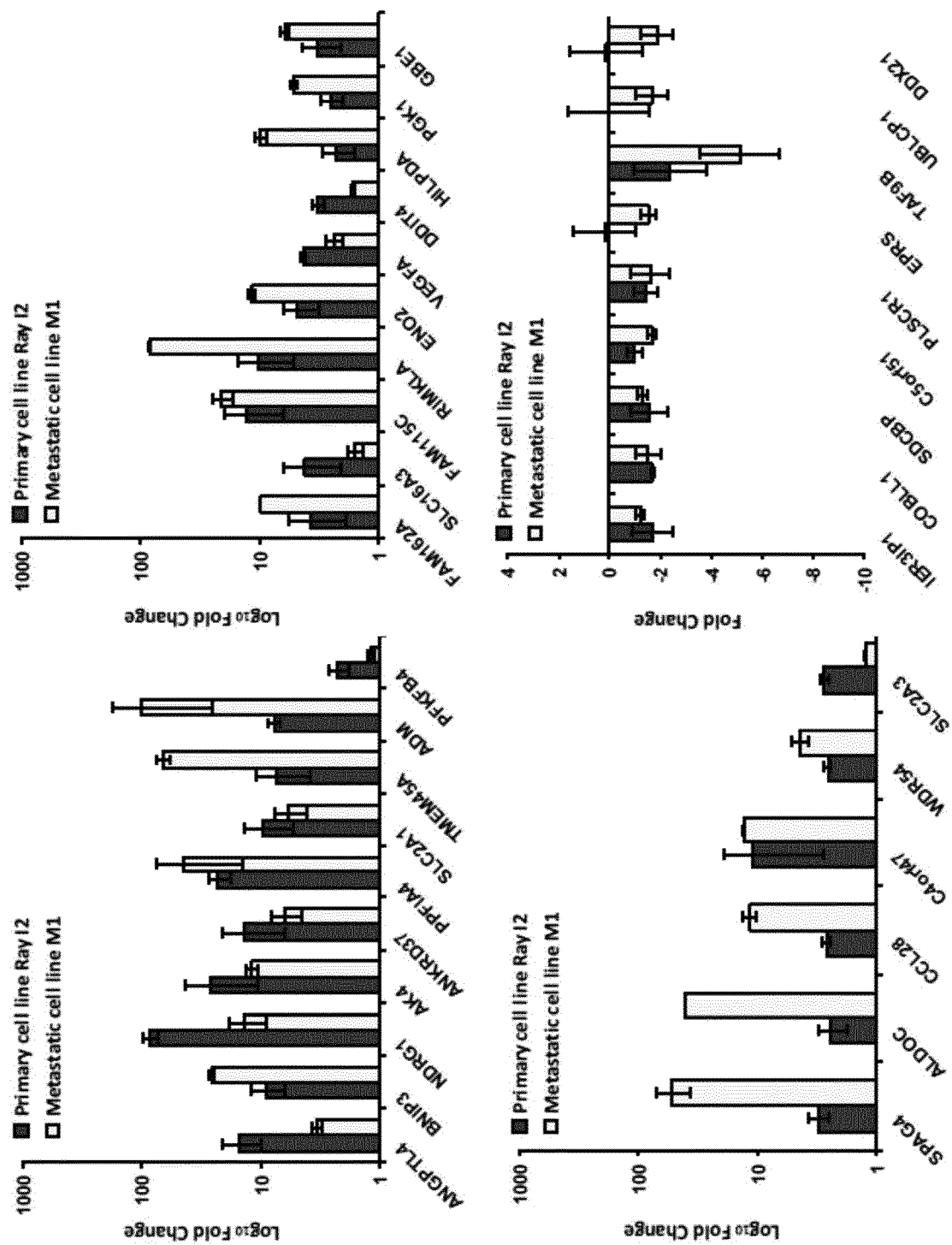
Figure 2B:
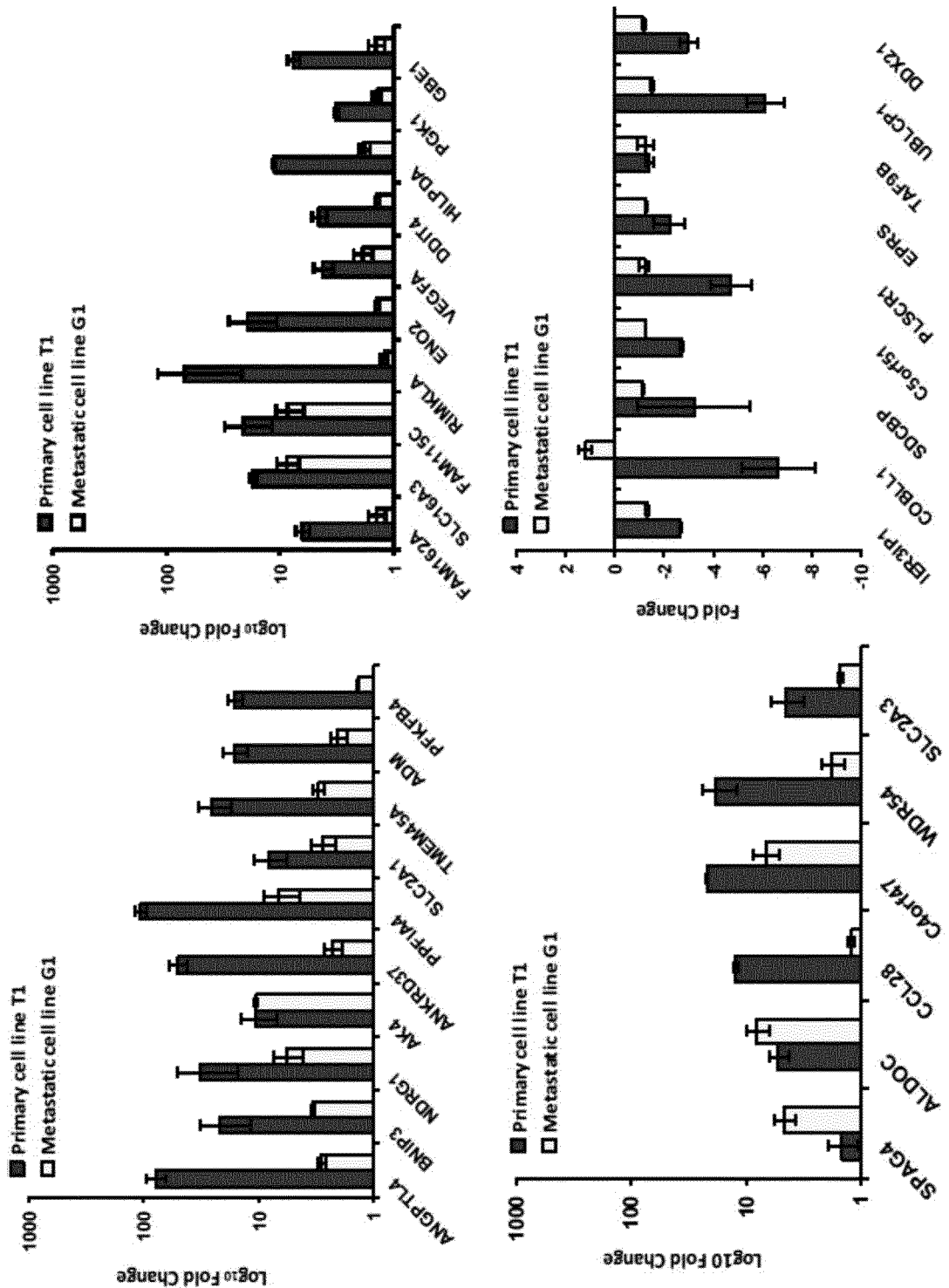
Figure 2C:
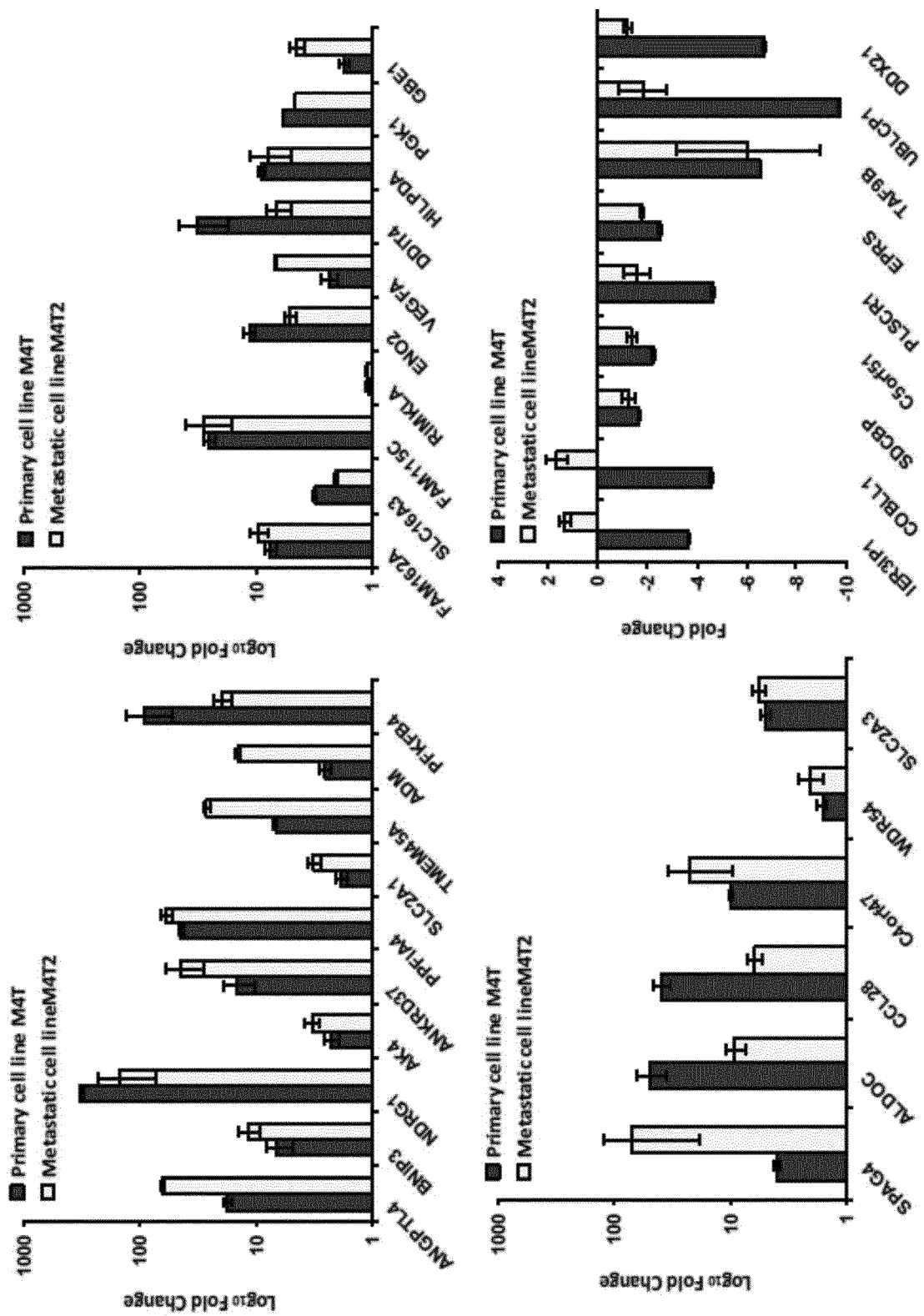
Figure 2D:
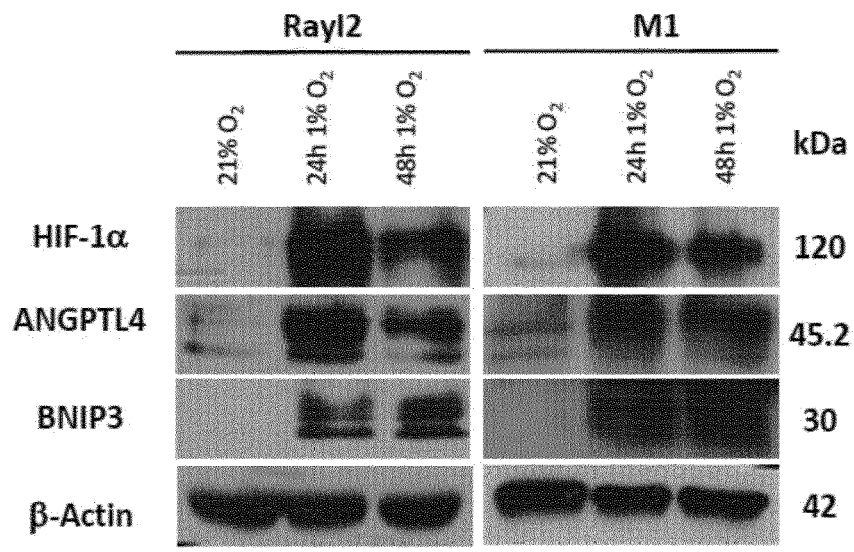
Figure 2E:
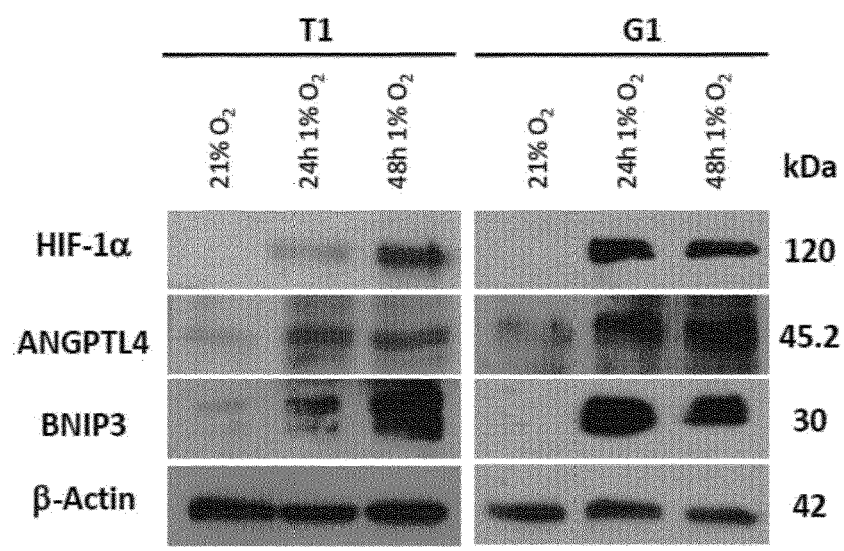
Figure 2F:
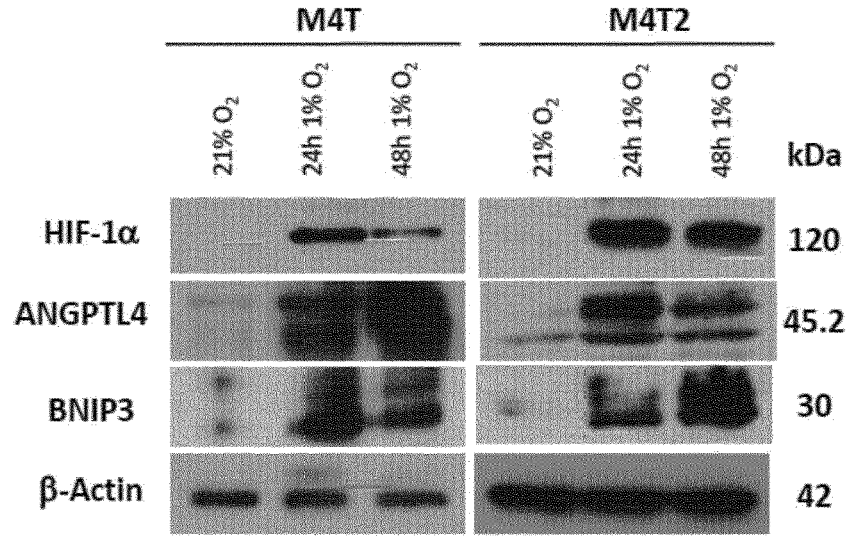
Figure 3A:
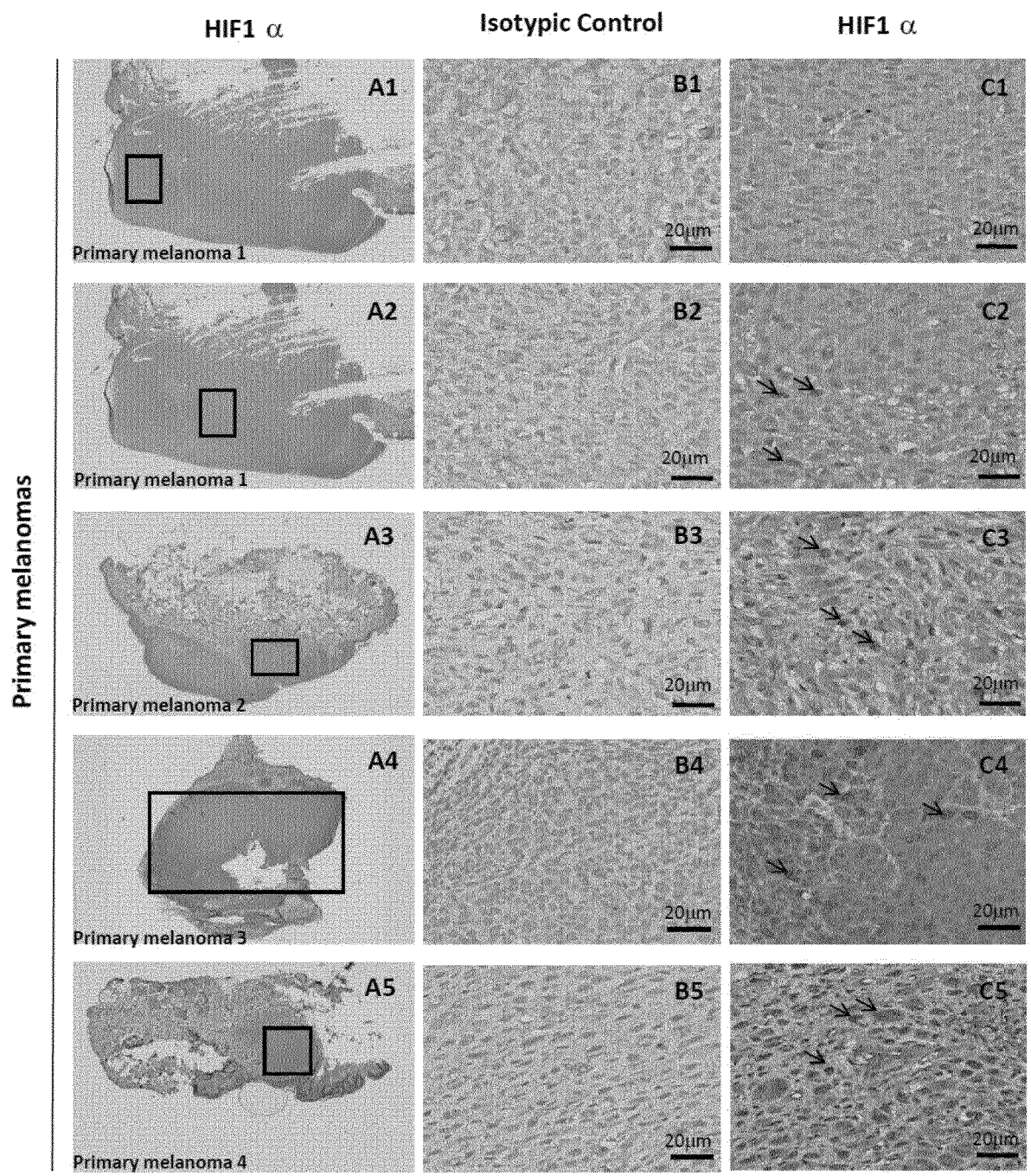
Figure 3D:
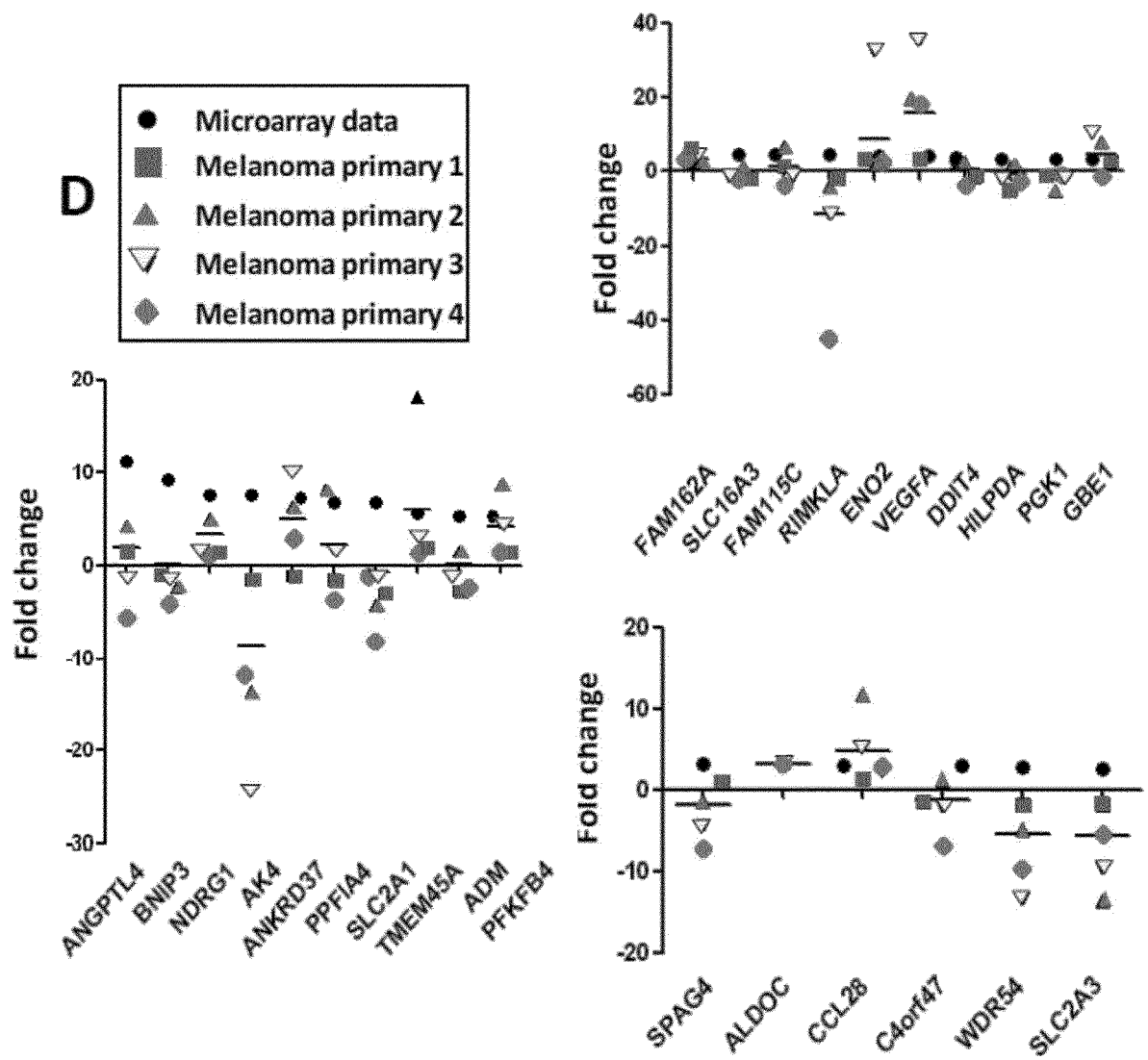
Figure 3E:
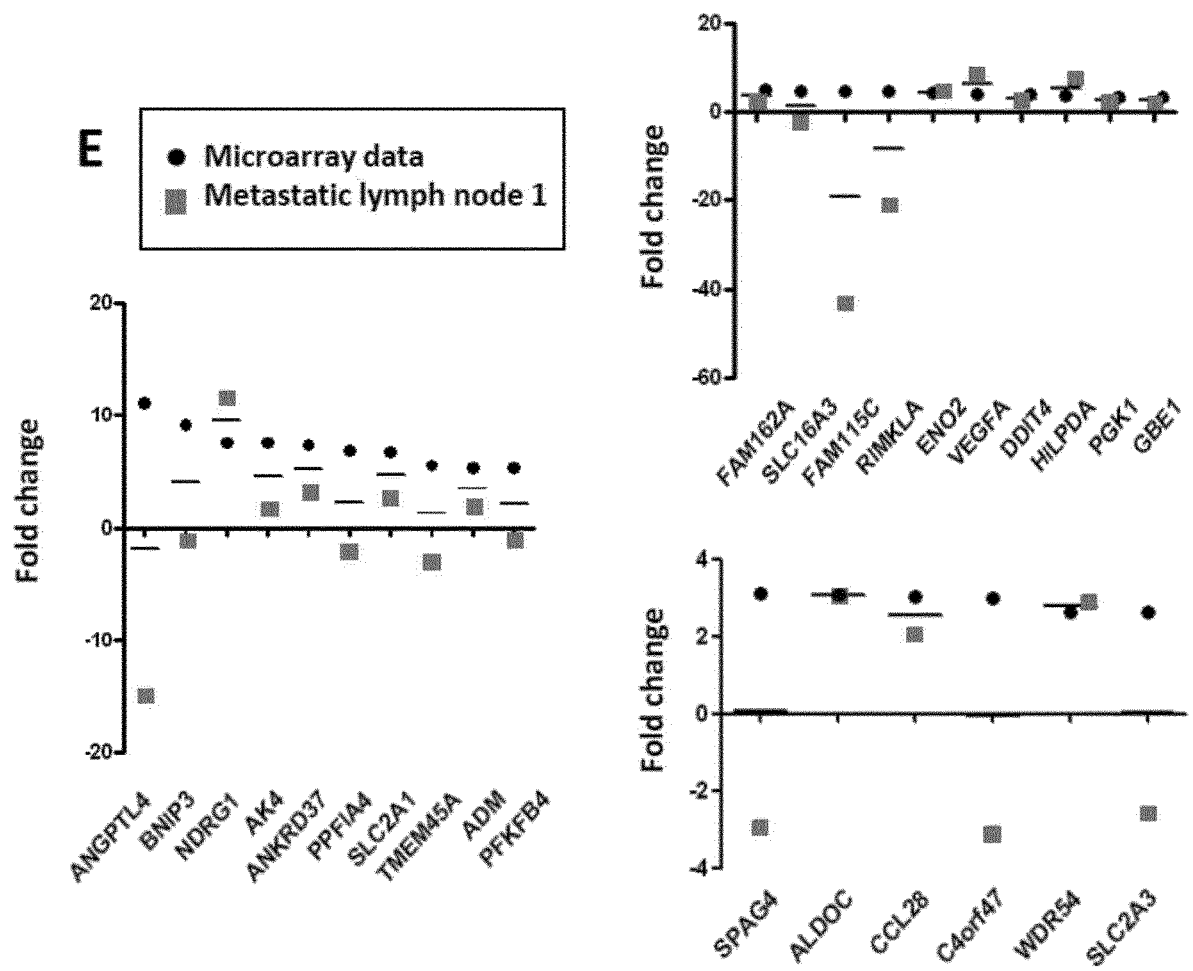
Figure 3F:
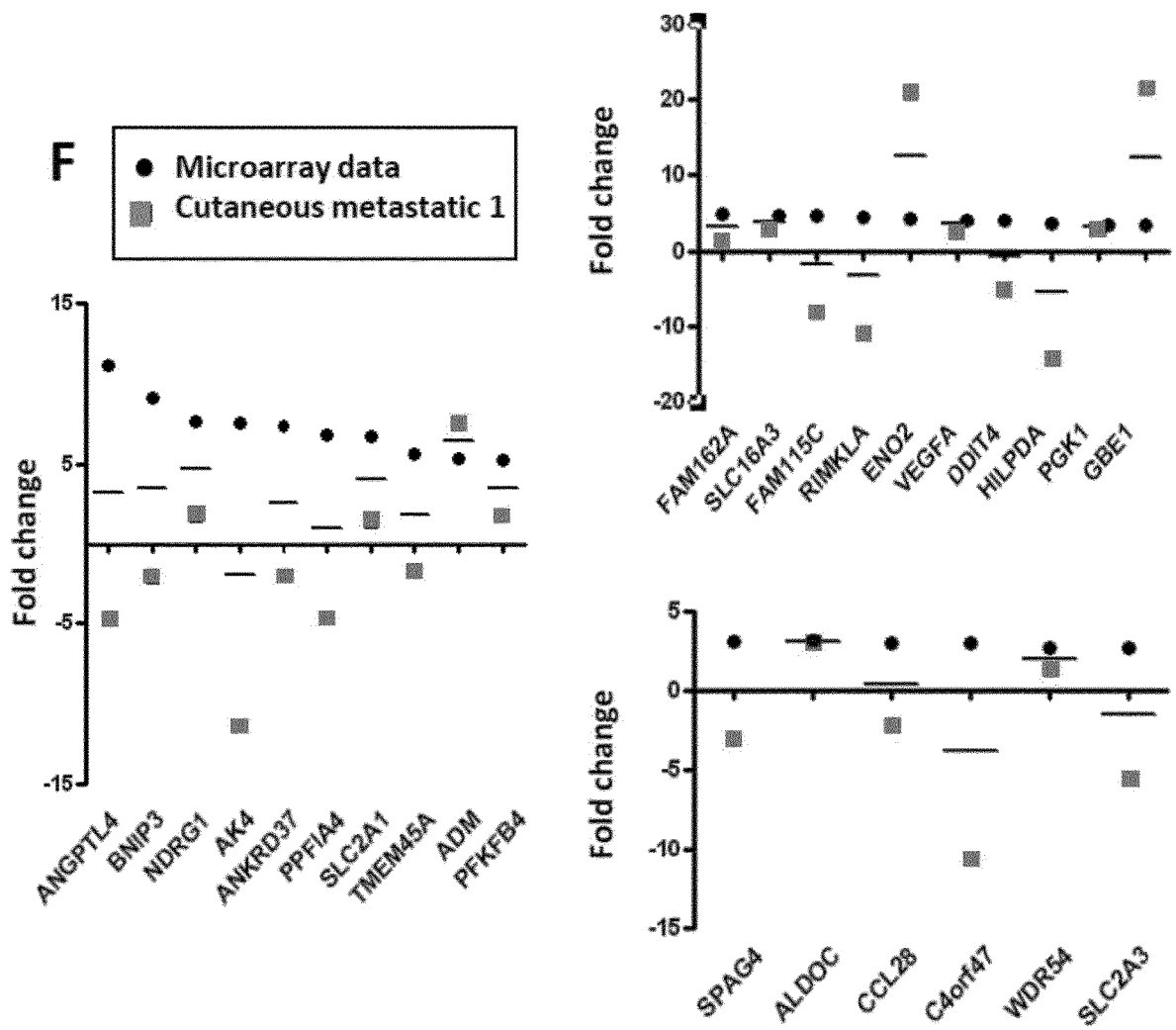

Comparative Analysis of Hypoxia Associated Gene Expression in Primary and Metastatic Melanoma:

The inventors next examined the gene expression response to hypoxic stress among freshly established melanoma cell lines and their metastatic counterpart (FIG. 2A, B, C). RTqPCR analysis was performed and a correlation fold change for microarray data and RT-qPCR data of two independent experiments was found.

The inventors have next performed western blot analysis on 3 highly expressed genes (HIF-1a, ANGPTL4 and BNIP3) under hypoxic conditions at 24 h and 48 h using primary melanoma cell lines and their metastatic counterparts. Data shown in FIG. 2 (D, E and F) clearly indicate that a translational expression of 3 genes occurred in the 3 lines fitting with the microarray and PCR data analysis.

Hypoxia Associated Gene Expression in Hypoxic Zones Detected by Anti-HIFα Immunohistochemistry (IHC) in Melanoma Patients Using IHC, the inventors could identify (FIG. 3) non hypoxic (C1) and hypoxic zones (C2, C3, C4, C5) and zones delimited in rectangle in A1 to A5, in primary melanoma from 4 patients based on the detection of HIF1α on serial sections of FFPE tissues. A1 and A2 are the same primary melanoma with one hypoxic zone and one non hypoxic.

In FIG. 3; IHC on serial sections of FFPE tissues using HIF1a antibodies allowed the identification of hypoxic (C7 and C9) and non hypoxic (C6 and C8) zones, delimited in rectangle in A6 to A9 in 2 metastatic lymph nodes and 2 cutaneous metastases from 4 patients.

After laser or scalpel dissecting the hypoxic and non hypoxic area in melanoma samples from 8 patients who developed primary melanoma, metastatic lymph node, or cutaneous metastasis, RNA were extracted then amplified by RT-qPCR for the 26 genes up regulated of interest in tumor hypoxic zones delimited after immunohistostaining with anti HIF1α. The inventors could demonstrate that the high staining with anti HIF1α in tumor hypoxic zone correlated with high expression of genes of the hypomel signature in patients with primary melanomas, patients with metastatic lymph nodes—and patients with cutaneous metastases.

The recent application of the NanoString as a reliable gene expression analysis prompted the inventors to test whether the expression of their selected genes was correlated to treatment response in melanoma patients treated with anti-PD1. The NanoString approach offers a valuable alternative to qPCR and the present data suggest that results are also accurate and need less materials because of direct quantification of gene copy number without the need for enzymatic amplification. The data obtained by microarray and nanostring correlate with a significant p value (p value of 0.00835, FIG. 4A) and reinforce the robustness of the method and results. So, the data prompted the inventors to further explore the quantitative NanoString technology to investigate whether some genes within the signature could have a predictive value for the clinical outcome. For this purpose, they identified 18 pairs of highly correlated pairs (correlation level>0.80) based on the raw expression levels of the 26 studied genes. NMF was applied on the resulting differential pairs, after proper transformation of the matrix to comply with the non-negativity assumption (see methods). The NMF-based ordering of samples appeared significantly associated with the responder status (p=0.0069 based on 1000 permutations). The dual ordering of genes pointed to the BNIP/GBE1 differential pair, which had the largest leverage on the second cluster. Responder status appeared significantly associated to BNIP/GBE1 differential expression level (p: 0069) following a one-way analysis of the differential pair (FIGS. 4B and 4C).

Discussion:

Based on the evidence currently available it now appears likely that both the adaptive and innate immune systems can recognize and eliminate tumours. The problem we face, however, is that the tumor microenvironment is able to neutralize and paralyze both responses. One challenge for tumour immunologists in the future is identifying patients for which immunotherapy will be efficacious. Accordingly, in the course of these studies, the inventors looked for pairs of highly correlated genes based on their raw expression levels (correlation level>0.80). Non-Negative Matrix Factorization, NMF, was applied to the split matrix (Jacobs et al. Int J Cell Biol 2012; 2012:930710), yielding a dual clustering of samples and genes into two clusters. Samples and genes were ordered by decreasing leverage on their respective cluster. Finally, the association between the ordering of samples and responder status was assessed through a permutation test. Specifically, responder status was permuted among patients, the association score re-calculated and compared to the original score.

The inventors identified 18 pairs of highly correlated pairs (correlation level>0.80) based on the raw expression levels of the 30 studied genes. The dual ordering of genes pointed to the BNIP/GBE1 differential pair, which had the largest leverage on the second cluster. Responder status appeared significantly associated to BNIP3/GBE1 expression ratio following a one-way analysis of the differential pair. The inventors could demonstrate that the relative levels of BNIP3 vs GBE1 correlate with the clinical outcome of melanoma patients treated anti-PD1 (nivolumab).

Material and Methods.

Clinical Samples

Clinical samples were collected from patients after having given their written informed consent in accordance with the declaration of Helsinki.

Human Tumor Melanoma Cell Lines and PBMC.

Human melanoma cell lines ME204 AI/ER, ME260 LN/DG, T921 DUF/ALE, ME300PB, ME290mH and NA8 derived from the primary lesion, were provided by Dr Pedro Romero (Ludwig Center for Cancer Research, Lausanne, Switzerland). M74 derived from the primary lesion was established by Pr Jotereau (CRCNA, Inserm UMR892, Nantes, France). RIOUP2 was derived from the primary lesion, by the laboratory. The 3 couple of 2 human melanoma cell lines: T1 and G1, M4T and M4T2, RAYI2 and M1 were derived respectively, from the primary lesion and the metastatic lymph node of 3 patients by the laboratory. All the melanoma cells were cultured in RPMI 1640 with glutamax supplemented with 10% FCS, 1% penicillin-streptomycin, 1% sodium pyruvate at 37° C. in a humidified atmosphere containing 5% CO2.

PBMC were generated from one healthy donor and cultivated in RPMI 1640 with glutamax supplemented with IL-2 (25 U/ml), 10% Human AB serum, 1% penicillin-streptomycin, 1% sodium pyruvate at 37° C. in a humidified atmosphere containing 5% C02.

Hypoxic Conditioning of Tumor Cells.

Hypoxic treatment was conducted in a hypoxia workstation (Invivo2400, Ruskinn) in a humidified atmosphere containing 5% Co2, 1% 02 and 94% N2 at 37° C. (24 h and 48 h). Melanoma cells for RNA and protein analysis were lysing directly in the hypoxia workstation without reoxygenated during the kinetic of hypoxia.

Microarray Assay.

Gene expression analysis were performed with Agilent® SurePrint G3 Human GE 8×60K Microarray (Agilent Technologies, AMADID 28004) with the following dual-color design: the test samples (Hypoxic samples) were labeled with Cy5 whereas the control samples (normoxic samples) were labeled in Cy3 using the two-color Agilent labeling kit (Low Input Quick Amp Labeling Kit 5190-2306) adapted for small amount of total RNA (100 ng total RNA per reaction). Hybridization were then performed on microarray using 825 ng of each linearly amplified cRNA labelled Cy3 or Cy5 sample, following the manufacturer protocol (Agilent SureHyb Chamber; 1650 ng of labeled extract; duration of hybridization of 17 hours; 40 µL per array; Temperature of 65° C.). After washing in acetonitrile, slides were scanned by using an Agilent G2565 C DNA microarray scanner with defaults parameters (100° PMT, 3 µm resolution, at 20° C.) in free ozone concentration environment. Microarray images were analysed by using Feature Extraction software version (10.7.3.1) from Agilent technologies. Defaults settings were used.

Microarray Data Processing and Analysis.

Raw data files from Feature Extraction were imported into R with LIMMA (Smyth, 2004, Statistical applications in Genetics and molecular biology, vol 3, No 1, article 3), an R package from the Bioconductor project, and processed as follow: gMedianSignal and rMedianSignal data were imported, controls probes were systematically removed, and flagged probes (glsSaturated, glsFeatpopnOL, glsFeatNonUnifOL, rlsSaturated, rlsFeatpopnOL, rlsFeatNonUnifOL) were set to NA. Intra-array normalization was performed by a loess normalization, followed by a quantile normalization of both Cy3 and Cy5 channel. Then inter-array normalization was performed by quantile normalization on M values. To get a single value for each transcript, taking the mean of each replicated probes summarized data. Missing values were inferred using KNN algorithm from the package 'impute' from R bioconductor.

Normalized data were then analyzed. To assess differentially expressed genes between two groups, we start by fitting a linear model to the data. Then we used an empirical Bayes method to moderate the standard errors of the estimated log-fold changes. The top-ranked genes were selected with the following criteria: an absolute fold-change≥2.5 and ≤−2 and an adjusted p-value (FDR)<0.005.

RNA Isolation and Real-Time Quantitative Polymerase Chain Reaction (RT-qPCR).

Total RNA was extracted from cell samples using TRIzol solution (Invitrogen). The quality of RNAs was assessed using a Bioanalyzer instrument (Agilent) and then quantified using a Biospecnano (Shimadzu). cDNA synthesis was prepared from 1 µg of total RNA with random hexamers using Applied Biosytems Reverse Transcription kit according to the supplied protocols. Gene expression was quantified by SYBR Green qPCR method (Applied Biosystems) using the Maxima™ SYBR Green/ROX qPCR Master Mix (ThermoFisher Scientific). Relative expression was calculated by using the comparative $C_t$ method (2-ΔΔCt). Primer sequences for the quantification of 35 genes were purchased from Sigma and are available upon request. Transcript levels of HPRT for PBMC, or 18S for melanoma cells lines were used as endogenous control.

Western Blot

Melanoma cells lines from 3 were grown in two different conditions normoxia (21% $PO_2$) and hypoxia (1% $PO_2$) for 24 h and 48 h at 37° C. Tumor cells were washed twice in phosphate-buffered saline and lysed in plates with lysis buffer (62.5 mM Tris-HCl [pH 6.8], 2% weight/volume sodium dodecyl sulfate, 10% glycerol, 1 mM orthovanadate, 2 mM phenylmethylsulfonyl fluoride, 25 µM leupeptin, 5 mM benzamidine, 1 µM pepstatin, and M aprotinin). Lysates were sonicated on ice, resolved by sodium dodecyl sulfate-polyacrylamide gel electrophoresis (30 g/well), and transferred onto nitrocellulose membranes. After incubation in blocking buffer, the membranes were probed overnight at 4° C. with the indicated primary Abs. Primary antibodies (Abs) against HIF-1α, ANGPTL4, BNIP3 and β-Actin were purchased respectively from BD Biosciences, Sigma, Abcam and Sigma. The labeling was visualized using peroxidase-conjugated secondary Abs and an enhanced chemiluminescence kit (Amersham International). Blots were scanned and processed by Adobe Photoshop 7.0 software.

Immunohistochemistry staining for HIF1α.

The tissue collection was provided by Dr P. Vielh (Gustave Roussy, Villejuif, France) and composed of 4 human melanoma primary tumors, 2 human cutaneous metastasis tumors and 2 human melanoma metastasis lymph nodes.

For each patient, four micrometer sections of Fixed-Formaldehyde Paraffin Embedded (FFPE) melanoma human tumor were prepared and stained with HES by V. Marty. Deparaffinized tissue sections were treated with Antigen Retrieval Solution (made from citrate buffer, pH 8.0, concentrated 10×, T0010 Diapath). Tissue sections were then incubated with $H_2O_2$ 3% for 10 min and solution PowerVision IHC/ISH Super Blocking (PV6122, MM France) for 20 min. Histological slides were incubated over night at 4° C. with a polyclonal rabbit anti human HIF1 antibody (NB100-479, Novus) or a rabbit polyclonal IgG (Ab 27472, Abcam). For signal amplification, slides were then incubated with rabbit alkaline phosphatase conjugated secondary antibody (PowerVision poly-AP anti-Rabbit IgG, PV3133, MM France). The signal was revealed with the Liquid Permanent Red (K0640, Dako) and Mayer's hemalun solution (HX390929, Merck) counterstain.

Laser Microdissection and Pressure Catapulting of Glomerules.

Laser microdissection was performed with a PALM® RoboSoftware 4.6 MicroBeam system (PALM Microlaser Technologies, Zeiss Micro-Imaging, Munich, Germany) coupled to an inverted microscope Axio Observer.Z1. Serial 20 µm-thick sections from 3 human melanoma FFPE* fragments (primary melanoma 1, 2 and 4, FIG. 3) were spread onto polyethylene naphthalate (PEN) membrane-coated slides (Carl Zeiss Micro Imaging, Munich, Germany). After sections the slide is incubated for 10 mn in a toluene solution followed by 10 mn in absolute alcohol to completely remove the paraffin embedding, Staining for 1 mn in a Mayer's Hematoxylin solution, 30 s in a saturated lithium carbonate solution and 30 s in a solution of erythrosine were successively done followed by 30 s each of absolute alcohol and toluene, respectively.

A total surface of 4 area (between $6.610^6$ µm² and $1810^6$ µm²) was collected from several sections representing the 3 identified hypoxic tumoral areas (zone A2, A3 and A5, FIG. 3) and 1 non hypoxic tumoral area (zone A1, FIG. 3). Microdissected control samples were done at the same time as an equivalent surface of the same tissue, but far away from the regions of interest. Each sample was recovered in lysis buffer from the RNeasy FFPE kit (Qiagen, Hilden, Germany) for further molecular analyses.

Macrodissection with Scalpel.

Serial 20 µm-thick sections from 5 human melanoma FFPE tumors (primary melanoma 4, metastatic lymph node 1 and 2, cutaneous metastasis 1 and 2, FIG. 3) were prepared as samples obtained by microdissection laser. A total of 5 area was collected with a scalpel from several sections representing the 3 identified hypoxic tumoral areas (zone A4, A7, and A9, FIG. 3) and 2 non hypoxic tumoral areas (zone A6 and A8, FIG. 3). Each sample was recovered in lysis buffer from the RNeasy FFPE kit (Qiagen, Hilden, Germany) for further molecular analyses.

Pathway Specific Gene Expression Profiling of Hypoxic and Non Hypoxic Tumoral FFPE Samples.

Total RNA was extracted from 9 area melanoma FFPE tissue sections obtained by microdissection laser or macrodissection with scalpel (zone A1 to A9, FIG. 3), using RNeasy FFPE kit (Qiagen, Hilden, Germany). RNA quantity and quality was assessed using the Nanodrop-ND-1000 (Nanodrop Technologies, Wilmington, USA). First-strand cDNA was synthesized using a High-Capacity cDNA Reverse Transcription Kit (Applied Biosystems, USA) according to the manufacturer's protocol.

Signaling pathways transcript analyses were conducted in duplicates using a personalised Human qPCR SignArrays® 384 system (gene profiling analysis Human qPCR SignArrays® 384 kit for 26 genes of interest; and Perfect Master-Mix SYBR Green® (AnyGenes®, France)) on a LightCycler 480 (Roche, France) as described by the manufacturer, in 9 FFPE samples. Quality control of qPCR data for consequent analysis was based on positive and negative PCR controls. Briefly, a total volume of 20111 of PCR mix, which included 1011 of Perfect MasterMix SYBR Green®, 8 µl of PCR grade water and 2 µl of cDNA was loaded into each well of the qPCR array. PCR amplification was conducted at 95° C. for 10 min, followed by 40 cycles of 95° C. for 10 sec and 60° C. for 30 sec. The mRNA expression for each gene was normalized using the average expression of 3 housekeeping genes: peptidylprolyl isomerase A (cyclophilin A, PPIA), b-actin (ACTB), and Glyceraldehyde-3-phosphate dehydrogenase (GAPDH). Data analysis was conducted using AnyGenes® Excel analysis tools based on ΔΔCt method by calculating fold changes for each gene as the difference in gene expression between HIF+ and HIF− samples.

Nanostring Analysis

Total RNA were extracted. 8 RNA samples already analysed by microarray and or, RT-qPCR, were included as controls in the analysis: 6 RNA sample from 3 cell lines (Mel-1, Mel-6 and Mel-10) cultured in normoxia and hypoxia, 1 RNA sample extracted from hypoxia FFPE zone positive of a primary melanoma (zone A4, FIG. 3) and 1 RNA sample extracted from hypoxia FFPE zone negative of a primary melanoma (zone A1, FIG. 3).

Total RNA concentration and purity (Ratio 260/280 and ratio 260/230 nm) were calculated using a Nanodrop ND8000 spectrophotometer (Ozyme, Saint-Quentin en Yvelines, France). Total RNA integrity was assessed using a micro electropheresys (RNA6000 LabChip, Agilent technologies, Les Ulis, France), and RIN or percentage of fragment longer than 300 nt were calculated, upon a total RNA migration. (table 1: Total RNA description)

Direct quantification of mRNA was achieved according a Nanostring Custom Elements approach. Briefly 50 ng of total RNA were used as template to detect 32 targets corresponding to 26 mRNA of interest and 6 housekeeping gene. The Nanostring Element chemistry was chosen for its flexibility because dedicated to small number of samples and small number of targets (see Worldwide Web site: nanostring.com/elements/tagsets). As this technology requires intermediate oligonucleotides (per targets a probe A and probe B are designed by Nanostring), long oligonucleotides specific to targets of interest were produced by IDT (Leuven, Belgium). Secondary oligonucleotides, complementary to 5' tail of first IDT long oligonucleotides, are biotinylated or coupled to reporter tag specific to each target. Those kits (Tagset) were ordered from Nanostring (Seattle, USA). A Universal Human RNA (Agilent technologies, Les Ulis, France) and water were also hybridized in parallel of samples of interest. Positive and negative controls were also added to samples as spike in controls. The Nanostring nSolver software was used to control raw data, and to normalize data based on geometric mean of positive controls, and water signals to deduce unspecific counts.

As an alternative to the above normalization scheme, the inventors looked for pairs of highly correlated genes based on their raw expression levels (correlation level>0.80), under the rationale that such correlated genes would normally share common biological properties yielding similar expression levels, however could differ in their response to treatment. Within each pair of correlated genes, the difference between genes, called "differential pair", was calculated, thereby ensuring that the variation in expression not caused by the response to treatment itself will be optimally filtered out. The matrix of differential pairs was further split into two parts corresponding to positive and negative differences. Within first part, negative differences were replaced by 0. Within second part, positive differences were replaced by 0, whereas negative differences were replaced by their absolute value. Non-Negative Matrix Factorization, NMF, was applied to the split matrix (Fogel et al., 2016], yielding a dual clustering of samples and genes into two clusters. Samples and genes were ordered by decreasing leverage on their respective cluster. Finally, the association between the ordering of samples and responder status was assessed through a permutation test. Specifically, responder status was permuted among patients, the association score re-calculated and compared to the original score.

TABLE 1

A list of hyposic signature (HYPOMEL) genes.

| Gene Name | Gene Bank* | Description |
| --- | --- | --- |
| ANGPTL4 | NM_139314 | Angiopoietin-like 4 |
| BNIP3 | NM_004052 | BCL2/adenovirus E1B 19 kDa interacting protein 3 |
| NDRG1 | NM_006096 | N-myc downstream regulated 1 |
| AK4 | NM_001005353 | Adenylate kinase 4, nuclear gene encoding mitochondrial protein |
| AHKRD37 | NM_181726 | Ankyrin repeat domain 37 |
| PPFIA4 | NM_015053 | Protein tyrosine phosphatase, receptor type, f polypeptide, interacting protein (liprin), alpha 4 |
| SLC2A1 | NM_006516 | Solute carrier family 2 (facilitated glucose transporter) |
| TMEM45A | NM_018004 | Transmembrane protein 45A |
| ADM | NM_001124 | Adrenomedullin |
| PFKFB4 | NM_004567 | 6-phosphofructo-2-kinase/fructose-2,6-biphosphatase 4 |
| FAM162A | NM_014367 | Family with sequence similarity 162, member A |
| SLC16A3 | NM_001042422 | Solute carrier family 16, members 3 |
| FAM115C | NM_173678 | Family with sequence similarity 115, member C |
| RIMKLA | NM_173642 | Ribosomal modification protein rimK-like family member A |
| ENO2 | NM_001975 | Enolase 2 (gamma, neuronal) |
| VEGFA | NM_001025366 | Vascular endothelial growth factor A |
| DDIT4 | NM_019058 | DNA-damage-inducible transcript4 |
| HILPDA | NM_013332 | Chromosome 7 open reading frame 68 |
| PGK1 | NM_000291 | Phosphoglycerate kinase 1 |
| GBE1 | NV_000158 | Glucan (1,4-alpha-), branching enzyme 1 |
| SPAG4 | NM_003116 | Sperm associated antigen 4 |
| ALDOC | NM_005165 | Aldolase C, fructose-bisphosphate (ALDOC), mRNA |
| CCL28 | NM_148672 | Chemokine (C-C motif) ligand 28 |
| C4orf47 | NM_001114357 | Chromosome 4 open reading frame 47 |
| WDR54 | NM_032118 | WD repeat domain 54 |
| SLC2A3 | NM_006931 | Solute carrier family 2 (facilitated glucose transporter), member 3 |
| IER3IP1 | NM_016097 | immediate early response 3 interacting protein 1 |
| COBLL1 | NM_014900 | COBL-like 1 |
| SDCBP | NM_005625 | Syndecan binding protein (syntenin) |
| C5orf51 | NM_175921 | Chromosome 5 open reading frame 51 |
| PLSCR1 | NM_021105 | Phospholipid scramblase 1 |
| EPRS | NW_004446 | Glutamyl-prolyl-tRNA synthetase |
| TAF9B | NM_015975 | TATA box binding protein (TBP)-associated factor |
| UBLCP1 | NM_145049 | Ubiquitin-like domain containing CTD phosphatase 1 |
| DDX21 | NM_004728 | DEAD (Asp-Glu-Ala-Asp) box polypeptide 21 |

*Gene bank accession number

The invention claimed is:

1. A method for treating a subject having a cancer with an anti-PD-1 antibody, wherein the method comprises:
    a) determining the expression level of BNIP3 and GBE1 in a cancer sample of the subject,
    b) determining a relative expression ratio of BNIP3 to GBE1,
    c) comparing the relative expression ratio of BNIP3 to GBE1 to a relative expression ratio of BNIP3 to GBE1 of a reference, thereby determining if the relative expression ratio of BNIP3 to GBE1 is indicative of a good responder or a poor responder to a treatment with the anti-PD-1 antibody, and
    d) administering the anti-PD-1 antibody to a subject having a relative expression ratio of BNIP3 to GBE1 that indicates that the subject is a good responder to treatment with said anti-PD-1 antibody,
    wherein a relative expression ratio of BNIP3 to GBE1 higher than the relative expression ratio of BNIP3 to GBE1 of the reference is indicative of a poor responder to a treatment with the anti-PD-1 antibody and a relative expression ratio of BNIP3 to GBE1 lower than the relative expression ratio of BNIP3 to GBE1 of the reference is indicative of a good responder to a treatment with the anti-PD-1 antibody,
    wherein the anti-PD-1 antibody is nivolumab and the cancer is melanoma.

2. The method according to claim 1, wherein the method further comprises a step of providing a sample from said subject.

3. The method according to claim 1, wherein the expression level of BNIP3 and GBE1 is determined by measuring the quantity of the mRNA transcripts.

4. A method of treating a subject having cancer comprising administering an anti-PD-1 antibody to a subject that has a relative expression ratio of BNIP3 to GBE1 which indicates the subject is a good responder to a treatment with said anti-PD-1 antibody, wherein a relative expression ratio of BNIP3 to GBE1 higher than the relative expression ratio of BNIP3 to GBE1 of a reference is indicative of a poor responder to a treatment with the anti-PD-1 antibody and a relative expression ratio of BNIP3 to GBE1 lower than the relative expression ratio of BNIP3 to GBE1 of a reference is indicative of a good responder to a treatment with the anti-PD-1 antibody, wherein the anti-PD-1 antibody is nivolumab and the cancer is melanoma.

5. The method according to claim 4, wherein the relative expression ratio of BNIP3 to GBE1 is determined by comparing expression levels of the relative expression ratio of BNIP3 to GBE1 in the cancer sample to the relative expression ratio of BNIP3 to GBE1 in a normal sample.

6. The method according to claim 1, wherein the relative expression ratio of BNIP3 to GBE1 is determined by comparing expression levels of BNIP3 to GBE1 in the cancer sample to the expression levels of BNIP3 to GBE1 in a normal sample.

7. The method according to claim 3, wherein the expression levels of BNIP3 to GBE1 is determined by quantitative RT-PCR, real time quantitative RT-PCR, nanostring technology PCR or by high-throughput sequencing technology.

8. The method according to claim 5, wherein the expression levels of BNIP3 to GBE1 is determined by quantitative RT-PCR, real time quantitative RT-PCR, nanostring technology PCR or by high-throughput sequencing technology.

* * * * *

UNITED STATES PATENT AND TRADEMARK OFFICE
CERTIFICATE OF CORRECTION

PATENT NO. : 11,293,066 B2
APPLICATION NO. : 16/631848
DATED : April 5, 2022
INVENTOR(S) : Salem Chouaib et al.

It is certified that error appears in the above-identified patent and that said Letters Patent is hereby corrected as shown below:

In the Specification

Column 12,
Line 35, "(1% 02)." should read --(1% $O_2$).--.

Column 17,
Line 28, "(30 g/well)," should read --(30µg/well),--.
Line 52, "HIF1" should read --HIF1α--.

Column 18,
Line 49, "20111" should read --20µl--.
Line 50, "1011" should read --10µl--.

Signed and Sealed this
Thirty-first Day of January, 2023

Katherine Kelly Vidal
Director of the United States Patent and Trademark Office